US012680895B2

(12) United States Patent
Collins et al.

(10) Patent No.: US 12,680,895 B2
(45) Date of Patent: Jul. 14, 2026

(54) SURGICAL DEVICE WITH REMOVABLY COUPLED COMPONENTS

(71) Applicant: Covidien LP, Mansfield, MA (US)

(72) Inventors: Ethan Collins, Naugatuck, CT (US); John Hryb, Southington, CT (US); Anthony Calderoni, Bristol, CT (US); John Pantazis, Stratford, CT (US)

(73) Assignee: Covidien LP, Mansfield, MA (US)

( * ) Notice: Subject to any disclaimer, the term of this patent is extended or adjusted under 35 U.S.C. 154(b) by 895 days.

(21) Appl. No.: 17/898,530

(22) Filed: Aug. 30, 2022

(65) Prior Publication Data

US 2022/0412823 A1     Dec. 29, 2022

Related U.S. Application Data

(60) Continuation of application No. 16/240,059, filed on Jan. 4, 2019, now Pat. No. 11,428,591, which is a
(Continued)

(51) Int. Cl.
*G01L 5/00*          (2006.01)
*A61B 17/072*        (2006.01)
(Continued)

(52) U.S. Cl.
CPC ...... *G01L 5/0028* (2013.01); *A61B 17/07207* (2013.01); *A61B 90/98* (2016.02); *A61B 2017/00398* (2013.01); *A61B 2017/00473* (2013.01); *A61B 2017/07278* (2013.01); *A61B 2090/064* (2016.02)

(58) Field of Classification Search
CPC . A61B 17/068; A61B 17/0682; A61B 17/072; A61B 17/07207; A61B 2017/00398; A61B 2017/0046; A61B 2017/00473; A61B 2017/00477; A61B 2017/00486; A61B 90/06; A61B 2090/064; A61B 2090/065; A61B 2090/066;
(Continued)

(56) References Cited

U.S. PATENT DOCUMENTS

| | | | |
|---|---|---|---|
| 3,039,303 A | 6/1962 | Reddick | |
| 3,358,257 A | 12/1967 | Painter et al. | |

(Continued)

FOREIGN PATENT DOCUMENTS

| | | | |
|---|---|---|---|
| AU | 2012312748 A1 | 4/2014 | |
| AU | 2014202295 A1 | 11/2014 | |

(Continued)

OTHER PUBLICATIONS

European Search Report dated Sep. 24, 2015, issued in European Application No. 15166107.
(Continued)

*Primary Examiner* — Todd J Scherbel

(57) ABSTRACT

A surgical instrument for applying fasteners includes a drive motor, a replaceable loading unit having an end-effector assembly, and an adapter configured to releaseably couple a replaceable loading unit to the drive motor. The adapter includes a strain gauge having a drive circuit coupled thereto. The strain gauge and the drive circuit are configured to directly measure a driving force in the adapter.

18 Claims, 32 Drawing Sheets

Related U.S. Application Data division of application No. 14/670,781, filed on Mar. 27, 2015, now Pat. No. 10,175,127.

(60) Provisional application No. 61/988,342, filed on May 5, 2014.

(51) Int. Cl.
*A61B 90/98* (2016.01)
*A61B 17/00* (2006.01)
*A61B 90/00* (2016.01)

(58) Field of Classification Search
CPC .... A61B 2562/0261; A61B 2562/0266; G01L 5/0028–0047
See application file for complete search history.

(56) References Cited

U.S. PATENT DOCUMENTS

| | | | |
|---|---|---|---|
| 3,920,082 | A | 11/1975 | Dudek |
| 4,006,784 | A | 2/1977 | Dudek |
| 4,043,222 | A | 8/1977 | Dudek |
| 4,281,538 | A | 8/1981 | Dudek |
| 4,404,799 | A | 9/1983 | Dudek |
| 5,155,423 | A | 10/1992 | Karlen et al. |
| 5,391,844 | A | 2/1995 | Johnson et al. |
| 5,460,182 | A | 10/1995 | Goodman et al. |
| 5,675,087 | A | 10/1997 | MacLaughlan et al. |
| 6,119,562 | A | 9/2000 | Jenkins |
| 6,360,615 | B1 | 3/2002 | Smela |
| 6,526,853 | B2 | 3/2003 | Jenkins |
| 6,872,187 | B1 | 3/2005 | Stark et al. |
| 7,335,053 | B2 | 2/2008 | Avevor et al. |
| 7,357,774 | B2 | 4/2008 | Cooper |
| 8,375,808 | B2 | 2/2013 | Blumenkranz et al. |
| 8,465,474 | B2 | 6/2013 | Blumenkranz |
| 8,613,230 | B2 | 12/2013 | Blumenkranz et al. |
| 8,621,939 | B2 | 1/2014 | Blumenkranz et al. |
| 8,678,979 | B2 | 3/2014 | Stark et al. |
| 8,753,344 | B2 | 6/2014 | Smith et al. |
| 8,945,095 | B2 | 2/2015 | Blumenkranz et al. |
| 9,706,674 | B2 * | 7/2017 | Collins ................... H05K 7/06 |
| 10,175,127 | B2 | 1/2019 | Collins et al. |
| 10,631,423 | B2 * | 4/2020 | Collins ............ A61B 17/07207 |
| 11,428,591 | B2 | 8/2022 | Collins et al. |
| 2002/0152849 | A1 | 10/2002 | Jenkins |
| 2005/0021050 | A1 | 1/2005 | Cooper |
| 2005/0101887 | A1 | 5/2005 | Stark et al. |
| 2006/0286861 | A1 | 12/2006 | Avevor et al. |
| 2007/0088340 | A1 | 4/2007 | Brock et al. |
| 2007/0151390 | A1 | 7/2007 | Blumenkranz et al. |
| 2007/0155588 | A1 | 7/2007 | Stark et al. |
| 2007/0214892 | A1 | 9/2007 | Turner et al. |
| 2009/0157092 | A1 | 6/2009 | Blumenkranz et al. |
| 2009/0248038 | A1 | 10/2009 | Blumenkranz et al. |
| 2010/0250000 | A1 | 9/2010 | Blumenkranz et al. |
| 2010/0313679 | A1 | 12/2010 | Larkin et al. |
| 2011/0017801 | A1 | 1/2011 | Zemlok et al. |
| 2011/0071553 | A1 | 3/2011 | Dlugos, Jr. et al. |
| 2011/0087212 | A1 | 4/2011 | Aldridge et al. |
| 2013/0079779 | A1 | 3/2013 | Smith |
| 2013/0150693 | A1 | 6/2013 | D'Angelo |
| 2013/0291654 | A1 | 11/2013 | Blumenkranz et al. |
| 2014/0012238 | A1 | 1/2014 | Chen et al. |
| 2014/0012289 | A1 | 1/2014 | Snow et al. |
| 2014/0088614 | A1 | 3/2014 | Blumenkranz |
| 2014/0107542 | A1 | 4/2014 | Schubert et al. |
| 2014/0110455 | A1 | 4/2014 | Ingmanson et al. |
| 2014/0137667 | A1 | 5/2014 | Blumenkranz et al. |
| 2014/0162242 | A1 | 6/2014 | Stark et al. |
| 2014/0207140 | A1 | 7/2014 | Smith et al. |
| 2015/0053749 | A1 * | 2/2015 | Shelton, IV ........... G16H 40/63 227/181.1 |
| 2016/0074038 | A1 | 3/2016 | Leimbach |

FOREIGN PATENT DOCUMENTS

| | | |
|---|---|---|
| CA | 2342357 A1 | 3/2000 |
| CA | 2828096 A1 | 8/2012 |
| CN | 1324260 | 11/2001 |
| CN | 103957824 | 7/2014 |
| DE | 69314358 T2 | 4/1998 |
| EP | 0738383 A1 | 10/1996 |
| EP | 0787980 A2 | 8/1997 |
| EP | 1109602 A2 | 6/2001 |
| EP | 2263592 A2 | 12/2010 |
| EP | 2280662 A1 | 2/2011 |
| EP | 2677987 A2 | 1/2014 |
| EP | 2684529 A2 | 1/2014 |
| EP | 2724674 A2 | 4/2014 |
| EP | 2757982 A1 | 7/2014 |
| FR | 2849589 A1 | 7/2004 |
| JP | 2011078772 A | 4/2011 |
| JP | 2015211832 A | 11/2015 |
| MX | 2014003504 | 7/2014 |
| WO | 9427125 A1 | 11/1994 |
| WO | 9837825 A1 | 9/1998 |
| WO | 2000012041 | 3/2000 |
| WO | 03026511 A1 | 4/2003 |
| WO | 2009123891 A1 | 10/2009 |
| WO | 2012116038 A2 | 8/2012 |
| WO | 2013043492 A1 | 3/2013 |
| WO | 2014201243 A2 | 12/2014 |

OTHER PUBLICATIONS

DeTemple, P., "Microtechnology in Modern Health Care", Med Device Technol. 9(9):18-25; (1998).
Abridged Data Sheet, "DeepCover Secure Authenticator with 1-Wire SHA-256 and 512-Bit User EEPROM", Maxim Integrated Products, Inc. pp. 1-4; 42; Dec. 2012.
Data Sheet "DS28E15-1-Sire SHA-256 Secure Authenticator with 512-Bit User EEPROM"; IC-On-line, Electronic Component Manufacturers, pp. 1-2; Aug. 2013.
U.S. Appl. No. 14/172,109, filed Feb. 4, 2014; inventor: Collins.
U.S. Appl. No. 14/287,651, filed May 27, 2014; inventor: Ma.
U.S. Appl. No. 14/459,008, filed Aug. 13, 2014; inventor: Ross.
European Office Action dated Jul. 5, 2018 in EP 15166107.
Chinese Office Action dated Jul. 23, 2018 in CN Appln. No. 2015102247766.
Australian Examination Report for application No. 2015201756 dated Feb. 27, 2019.
Japanese Office Action for applicatnoin b=No. 2015-088456 dated Nov. 26, 2018 with English translation.
Japanese Office Action issued in corresponding Appl. No. JP 2019-032605 mailed Jul. 2, 2020 (3 pages) together with English language translation (7 pages).
Canadian Office Action issued in corresponding application CA 2,887,955 dated May 14, 2021 (6 pages).

* cited by examiner

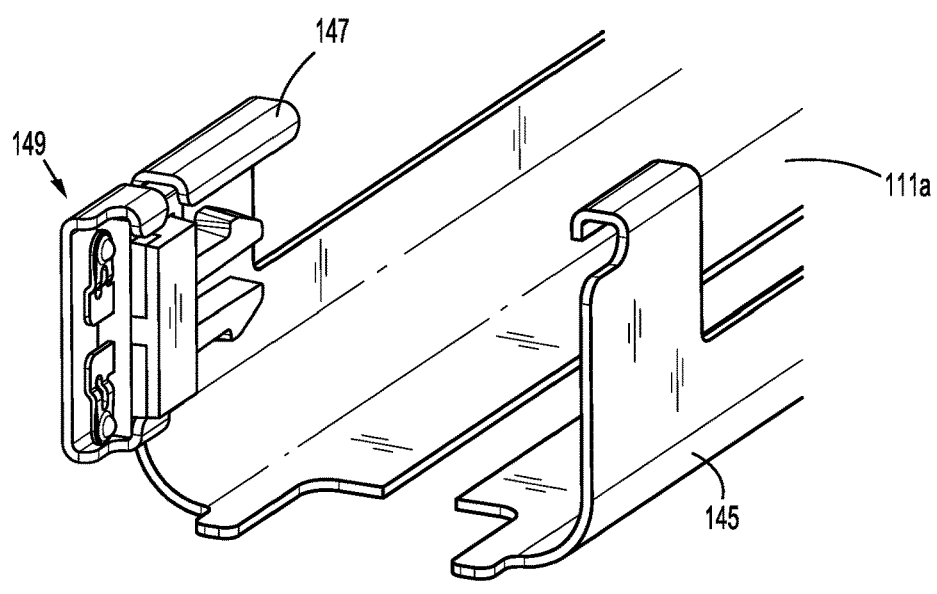
FIG. 29
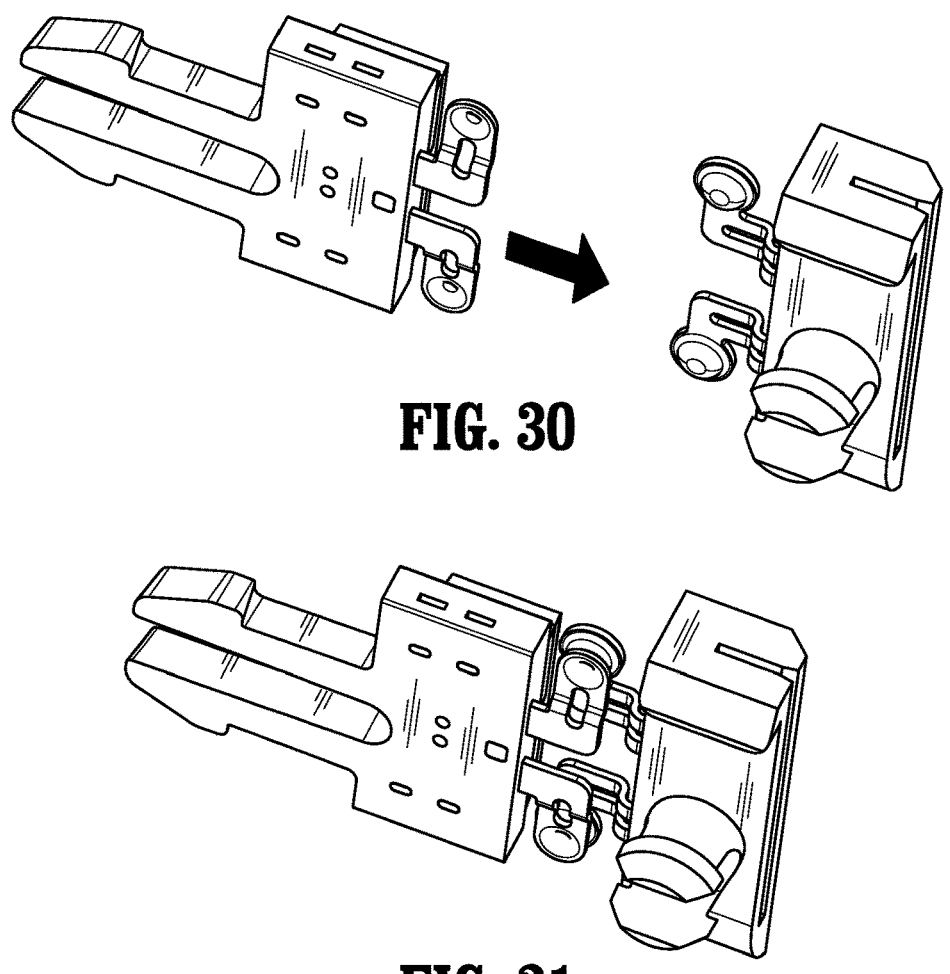
FIG. 30
FIG. 31

147a

120a

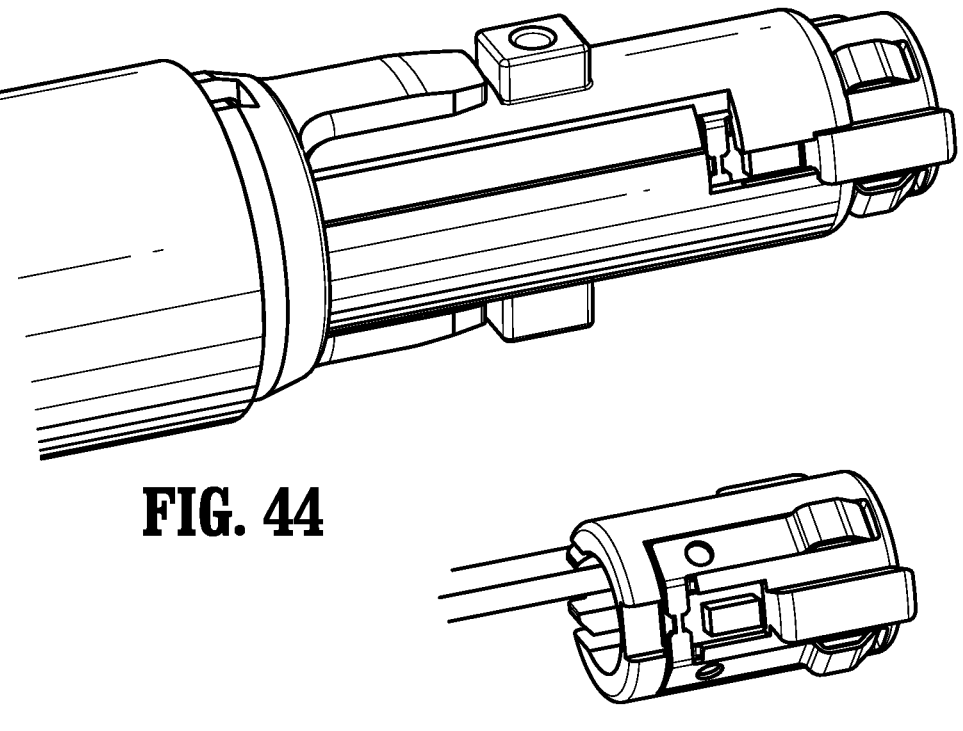
FIG. 44
FIG. 45
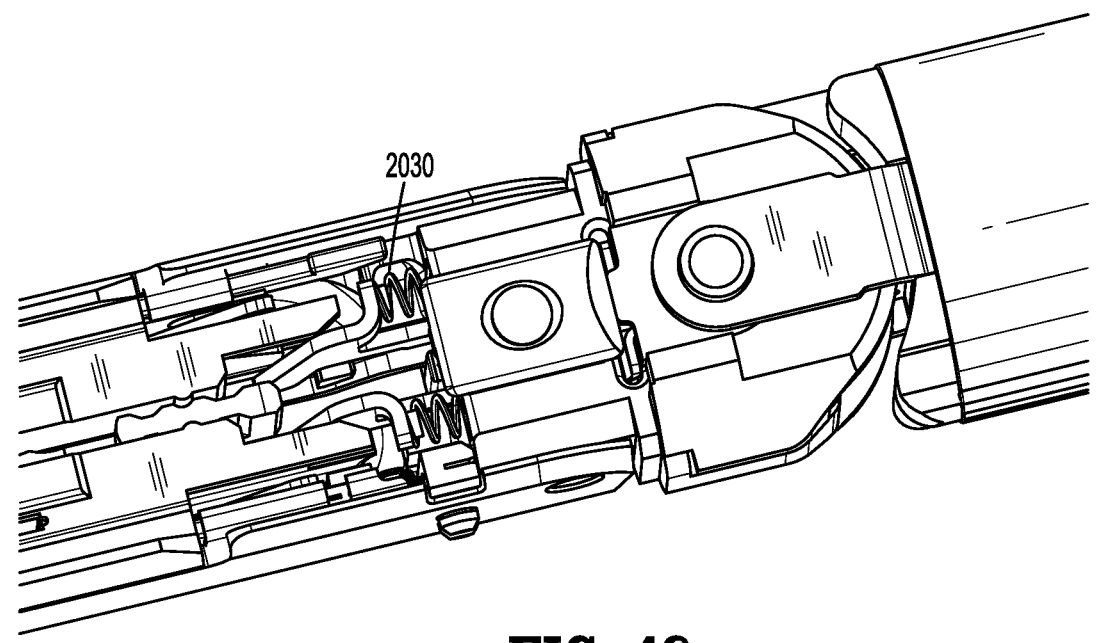
2030
FIG. 46

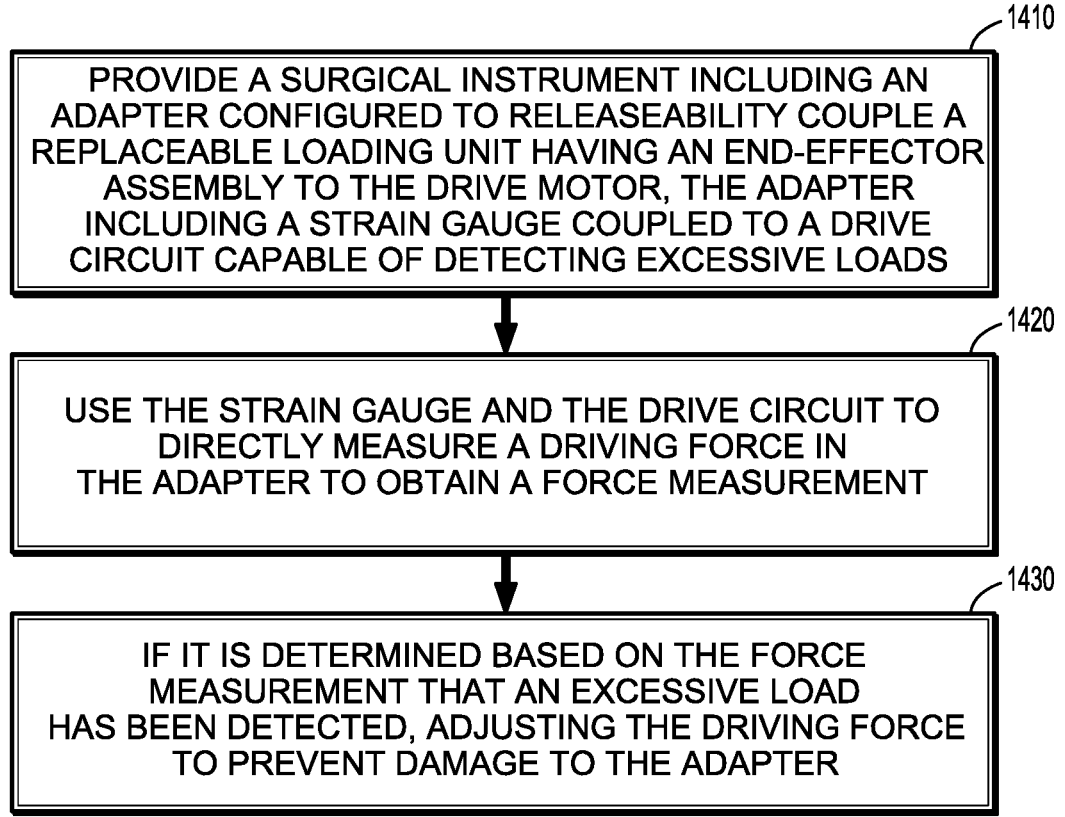

1410

PROVIDE A SURGICAL INSTRUMENT INCLUDING AN ADAPTER CONFIGURED TO RELEASEABILITY COUPLE A REPLACEABLE LOADING UNIT HAVING AN END-EFFECTOR ASSEMBLY TO THE DRIVE MOTOR, THE ADAPTER INCLUDING A STRAIN GAUGE COUPLED TO A DRIVE CIRCUIT CAPABLE OF DETECTING EXCESSIVE LOADS

1420

USE THE STRAIN GAUGE AND THE DRIVE CIRCUIT TO DIRECTLY MEASURE A DRIVING FORCE IN THE ADAPTER TO OBTAIN A FORCE MEASUREMENT

1430

IF IT IS DETERMINED BASED ON THE FORCE MEASUREMENT THAT AN EXCESSIVE LOAD HAS BEEN DETECTED, ADJUSTING THE DRIVING FORCE TO PREVENT DAMAGE TO THE ADAPTER

FIG. 61

SURGICAL DEVICE WITH REMOVABLY COUPLED COMPONENTS

CROSS-REFERENCE TO RELATED APPLICATIONS

This application is a continuation of U.S. patent application Ser. No. 16/240,059, filed on Jan. 4, 2019, now U.S. Pat. No. 11,428,591, which is a divisional of U.S. patent application Ser. No. 14/670,781, filed on Mar. 27, 2015, now U.S. Pat. No. 10,175,127, which claims the benefit of the filing date of provisional U.S. Patent Application No. 61/988,342, filed on May 5, 2014.

FIELD

The present disclosure relates to surgical devices having a reusable handle assembly and removable and replaceable components. More particularly, the present disclosure relates to an end-effector force measurement drive circuit suitable for use in a surgical instrument for applying fasteners.

BACKGROUND

Powered surgical instruments for use in endoscopic procedures are known. Typically, such instruments include a reusable handle assembly, and a replaceable and generally disposable component sometimes referred to as single use loading unit or SULU. An adapter assembly connects the loading unit, which can include an end effector for interacting with tissue, to the handle assembly. In the case of a surgical stapler, the end effector can include a replaceable cartridge that is changed after each firing of the surgical stapler. To reduce costs and shorten procedure times, the handle assemblies are generally configured for use with a variety of loading units and/or assemblies of various configurations for use on tissue having different properties, e.g., thickness and density. For example, the different loading units may have staples of different sizes and/or the staples may be arranged in different configurations. To ensure the handle assembly is programmed to operate with the attached loading unit, some loading units are provided with an integrated circuit, also known as a chip, that communicates with the handle assembly to identify the configuration of the loading unit. This arrangement enables the configuration of the loading unit to be automatically conveyed to the handle assembly upon attachment of the loading unit to the adapter assembly, thereby eliminating user error or incompatibility that may be experienced when switching between loading units with different configurations.

Surgical staplers are commonly used for stapling tissue within a body cavity where the end effector is likely to come in contact with fluids, e.g., blood, bile, and/or irrigation solutions. If the interconnections between the chip and the handle assembly are compromised, the chip could malfunction or data communications between the loading unit and the handle assembly could be disrupted, rendering the surgical stapler unstable or inoperable.

Printed circuit boards (PCBs), sometimes referred to as printed wiring boards (PWBs) or etched wiring boards, are widely used in the assembly of discrete electrical components into operating circuits. PCBs generally provide a reliable and economical means of interconnecting electrical signals among system components. PCBs are available in a variety of different types and may be classified in a variety of ways.

PCBs are generally used to mechanically support and electrically connect electronic components using electrically-conductive pathways or signal traces that conduct signals on the PCB. A typical PCB includes one or more layers of insulating material upon which patterns of electrical conductors are formed. In addition to a pattern of conductive traces on the PCB, a patterned array of metal-filled through-holes, or vias, may be formed to allow for layer-to-layer interconnections among various conductive features. A PCB on which electrical components are mounted is sometimes referred to as a printed circuit assembly (PCA) or a printed circuit board assembly (PCBA).

Various kinds of electrosurgical devices that employ PCBs have become thin and/or compact. In some devices, the amount of space needed to accommodate the PCBs may make it difficult to reduce the size of the devices. In some cases, PCB layouts large enough to accommodate the electrical components needed to provide desired functionality and/or performance may increase the overall size of the device and potentially hinder usability.

Electrical signals may be used on PCBs for controlling the delivery of surgical staples to tissue. Surgical devices for applying staples, clips, or other fasteners to tissue are well known. Endoscopic surgical devices for applying surgical fasteners include an actuation unit, i.e., a handle assembly for actuating the device and a shaft for endoscopic access, and an end-effector assembly disposed at a distal end of the shaft. Certain of these devices are designed for use with a replaceable loading unit which includes the end-effector assembly and houses the staples or fasteners. The replaceable loading unit may include staples of various sizes and the staples may be arranged in one or more configurations. After firing the stapler with a replaceable loading unit, the user may remove the empty loading unit, select and attach to the stapler another loading unit having staples of the same or different size and the same or different staple arrangement, and fire the stapler again. This process may be performed repeatedly during a surgical procedure.

During a surgical procedure, when the end-effector assembly is clamping down on tissue, or firing, in some situations it may be unclear whether the end-effector assembly has hit a piece of cartilage, and the surgeon may not be sure if he wants to go further. In some cases, when the end-effector assembly has hit something that blocks it from firing or that the motor drive has to overcome, the instrument draws excessive current which can be detected and measured. However, motor current measurements may not be entirely reliable, such as when the end-effector assembly has hit another staple line or encountered a malformed series of staples.

SUMMARY

According to an aspect of the present disclosure, a surgical instrument for applying fasteners is provided and includes a drive motor, a replaceable loading unit having an end-effector assembly, and an adapter configured to releaseably couple the replaceable loading unit to the drive motor. The adapter includes a strain gauge having a drive circuit coupled thereto. The strain gauge and the drive circuit are configured to directly measure a driving force in the adapter.

According to another aspect of the present disclosure, a method of measuring a driving force in a surgical device includes providing a surgical instrument for applying fasteners including an adapter configured to releaseably couple a replaceable loading unit having an end-effector assembly to a drive motor. The adapter includes a strain gauge coupled to a drive circuit capable of detecting excessive loads. The method also includes using the strain gauge and the drive circuit to directly measure a driving force in the adapter to obtain a force measurement and if it is determined based on the force measurement that an excessive load has been detected, adjusting the driving force to prevent damage to the adapter.

According to any one of the preceding aspects, the drive circuit includes a microprocessor and factory-calibrated force measurements including slope and offset correction factors are permanently stored in the microprocessor of the drive circuit. According to any one of the preceding aspects, the drive circuit further includes a voltage regulation circuit configured to provide a DC voltage.

BRIEF DESCRIPTION OF THE DRAWINGS

The above and other aspects, features, and advantages of the present disclosure will become more apparent in light of the following detailed description when taken in conjunction with the accompanying drawings in which:

FIG. 4 is an enlarged view of the proximal end of the loading unit and the distal end of the adapter assembly shown in FIG. 3;

FIG. 5 is another enlarged view of the proximal end of the loading unit and the distal end of the adapter assembly shown in FIG. 3;

FIG. 29 is a detailed perspective view of a support plate in accordance with embodiments of the present disclosure;

FIG. 30 is a perspective view of the chip assembly and board assembly of FIGS. 25-28;

FIG. 31 is another perspective view of the chip assembly and board assembly of FIGS. 25-28;

FIG. 44 is a perspective view of the proximal portion of the loading unit;

FIG. 45 is another perspective view of the chip assembly;

FIG. 46 is a detailed perspective view of a lockout assembly in accordance with embodiments of the present disclosure;

FIG. 61 is a flowchart illustrating a method of measuring a driving force in a surgical device in accordance with an embodiment of the present disclosure.

DETAILED DESCRIPTION

Figure 1:
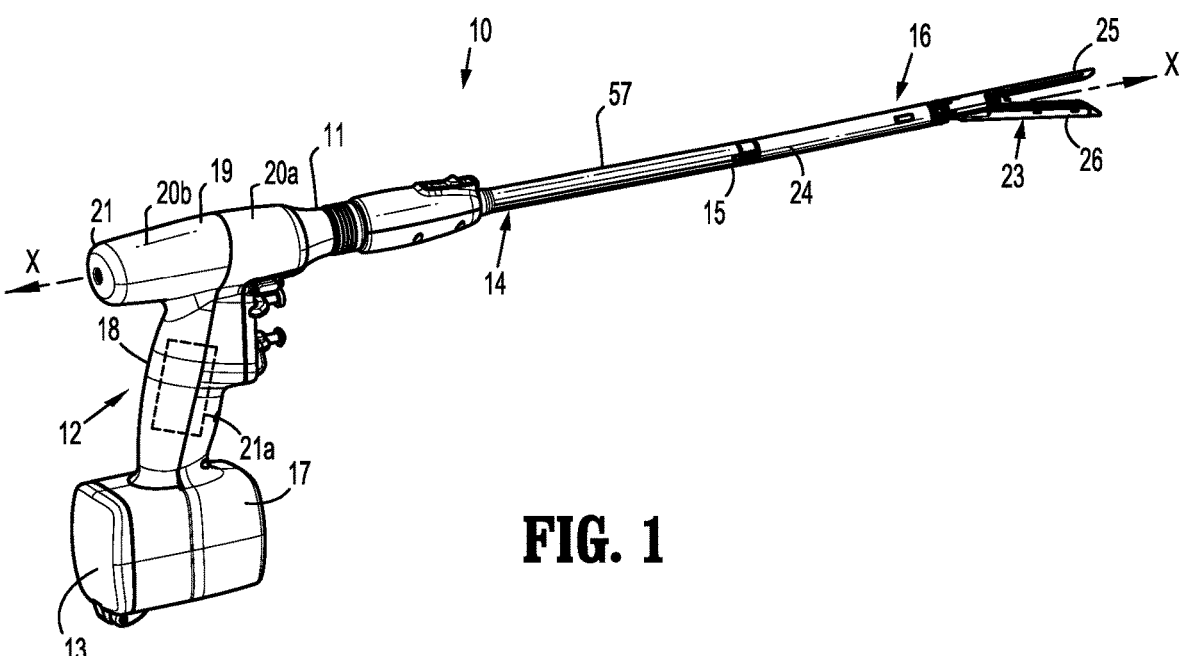
FIG. 1 is a perspective view of a surgical stapling device for use with a chip assembly according to embodiments of the present disclosure.

Hereinafter, embodiments of the presently-disclosed surgical instrument including an adapter configured with a strain gauge and a drive circuit and method of measuring a driving force in a surgical device are described with reference to the accompanying drawings. Like reference numerals may refer to similar or identical elements throughout the description of the figures. Particular embodiments of the present disclosure are described hereinbelow with reference to the accompanying drawings; however, it is to be understood that the disclosed embodiments are merely examples of the disclosure, which may be embodied in various forms. Well-known and/or repetitive functions and constructions are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. As is common in the art, the term "proximal" refers to that part or component closer to the user or operator, i.e. surgeon or clinician, while the term "distal" refers to that part or component further away from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions. Embodiments of the presently disclosed chip assembly will now be described in detail with reference to the drawings in which like reference numerals designate identical or corresponding elements in each of the several views. The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

This description may use the phrases "in an embodiment," "in embodiments," "in some embodiments," or "in other embodiments," which may each refer to one or more of the same or different embodiments in accordance with the present disclosure.

As used herein, the terms "power source" and "power supply" refer to any source of electrical power, e.g., electrical outlet, a/c generator, battery or battery pack, etc. As it is used in this description, "electrically conductive," or simply "conductive," generally refers to materials that are capable of electrical conductivity, including, without limitation, materials that are highly conductive, e.g., metals and alloys, or materials that are semi-conductive, e.g., semi-conducting materials and composites. As it is used in this description, "transmission line" generally refers to any transmission medium that can be used for the propagation of signals from one point to another.

Figure 2:
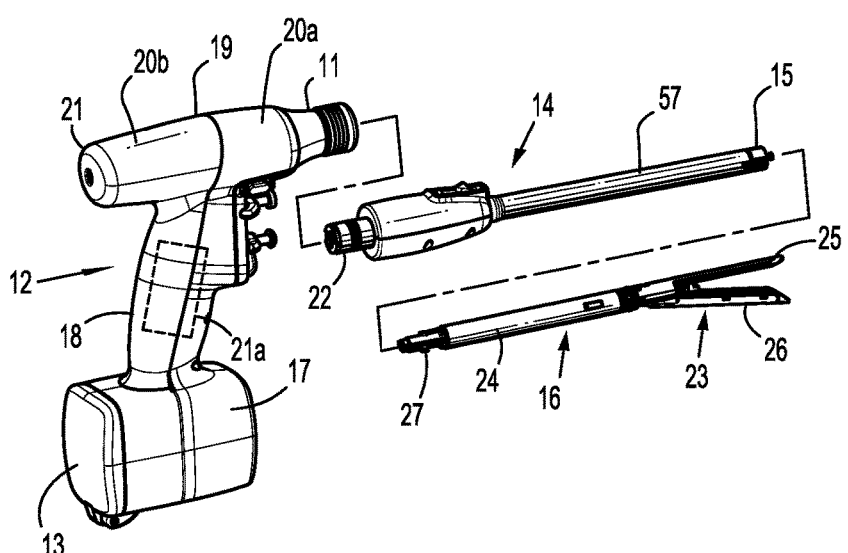
FIG. 2 is a perspective view of the surgical stapling device of FIG. 1 showing the handle assembly, adapter assembly, and loading unit in a separated configuration.

With reference initially to FIGS. 1 and 2, a surgical stapling instrument including an authentication system according to the present disclosure is shown generally as stapler 10. Stapler 10 includes a handle assembly 12, an adapter assembly 14 extending distally from handle assembly 12, and a loading unit 16 selectively secured to a distal end of adapter assembly 14. A detailed description of handle assembly 12, adapter assembly 14, and loading unit 16 is provided in commonly-owned U.S. Patent Appl. Publ. No. 2012/0089131, the contents of which is incorporated herein by reference in its entirety.

Handle assembly 12 includes a lower housing portion 17, an intermediate housing portion 18 extending from and/or supported on lower housing portion 17, and an upper housing portion 19 extending from and/or supported on intermediate housing portion 18. Intermediate housing portion 18 and upper housing portion 19 are separated into a distal half-section 20*a* that is integrally formed with, and extends from, the lower housing portion 17, and a proximal half-section 20*b* joined to distal half-section 20*a* by any suitable manner of attachment, such as without limitation, ultrasonic welding and/or a plurality of fasteners. When joined, distal and proximal half-sections 20*a*, 20*b* form a handle housing 21 defining a cavity therein which houses a circuit board that includes a controller 21*a*, and a drive mechanism (not shown).

Lower housing portion 17 includes a door 13 pivotally connected thereto for accessing a cavity formed in lower housing portion 17 for retaining a battery (not shown) therein. It is contemplated that stapler 10 may be powered by any number of power sources, such as, for example and without limitation, a fuel cell, a power cord connected to an external power source, and so forth.

Adapter assembly 14 includes a drive coupler 22 at a proximal end thereof and a loading unit coupler 15 at a distal end thereof. Distal half-section 20*a* of upper housing portion 19 defines a nose or connecting portion 11 configured to operably receive drive coupler 22 of adapter assembly 14. Loading unit 16 includes an adapter coupler 27 configured to operably receive loading unit coupler 15 of adapter assembly 14.

Upper housing portion 19 of handle housing 21 encloses a drive mechanism (not shown) configured to drive shafts and/or gear components (not shown) in order to perform the various operations of stapler 10. In particular, the drive mechanism is configured to drive shafts and/or gear components in order to selectively move a tool assembly or end effector 23 of loading unit 16 relative to a proximal body portion 24 of loading unit 16, to rotate loading unit 16 about a longitudinal axis "X-X" (FIG. 1) relative to handle housing 21, to move an anvil assembly 25 relative to cartridge assembly 26 of loading unit 16, and/or to fire a stapling and cutting cartridge within cartridge assembly 26 of loading unit 16.

The loading unit 16 shown in the FIGS. 1-21 is a linear surgical stapling loading unit. The loading unit includes a stapling anvil with recesses for forming surgical staples that are driven against it by operation of the loading unit in the surgical system. A staple cartridge houses the surgical staples, as well as the staple firing and/or driving assembly. The staple firing and/or driving assembly is known. One such assembly is described in U.S. Pat. Nos. 8,256,656 and 7,044,353, the entire disclosures of which are hereby incorporated by reference herein. The drive assembly includes an elongated drive beam having a knife blade. The drive beam pushes an actuation sled having wedge shaped surfaces for interacting with pushers. The pushers support the staples and have camming surfaces that the sled wedge shaped surfaces slide against, driving the pushers upwardly while the sled is advanced in a longitudinal fashion through the staple cartridge.

It is contemplated that the loading unit has jaw members for supporting the anvil and the staple cartridge respectively. The anvil jaw member and staple cartridge jaw member can be approximated to clamp tissue therebetween. It is also contemplated that the end effector can articulate or pivot off axis from the longitudinal axis defined by the proximal body portion 24.

It is contemplated that the loading unit can be a circular surgical stapling unit, other types of stapling units, or other types of surgical end effectors, such as electrocautery, ablation, ultrasonic, etc.

Figure 3:
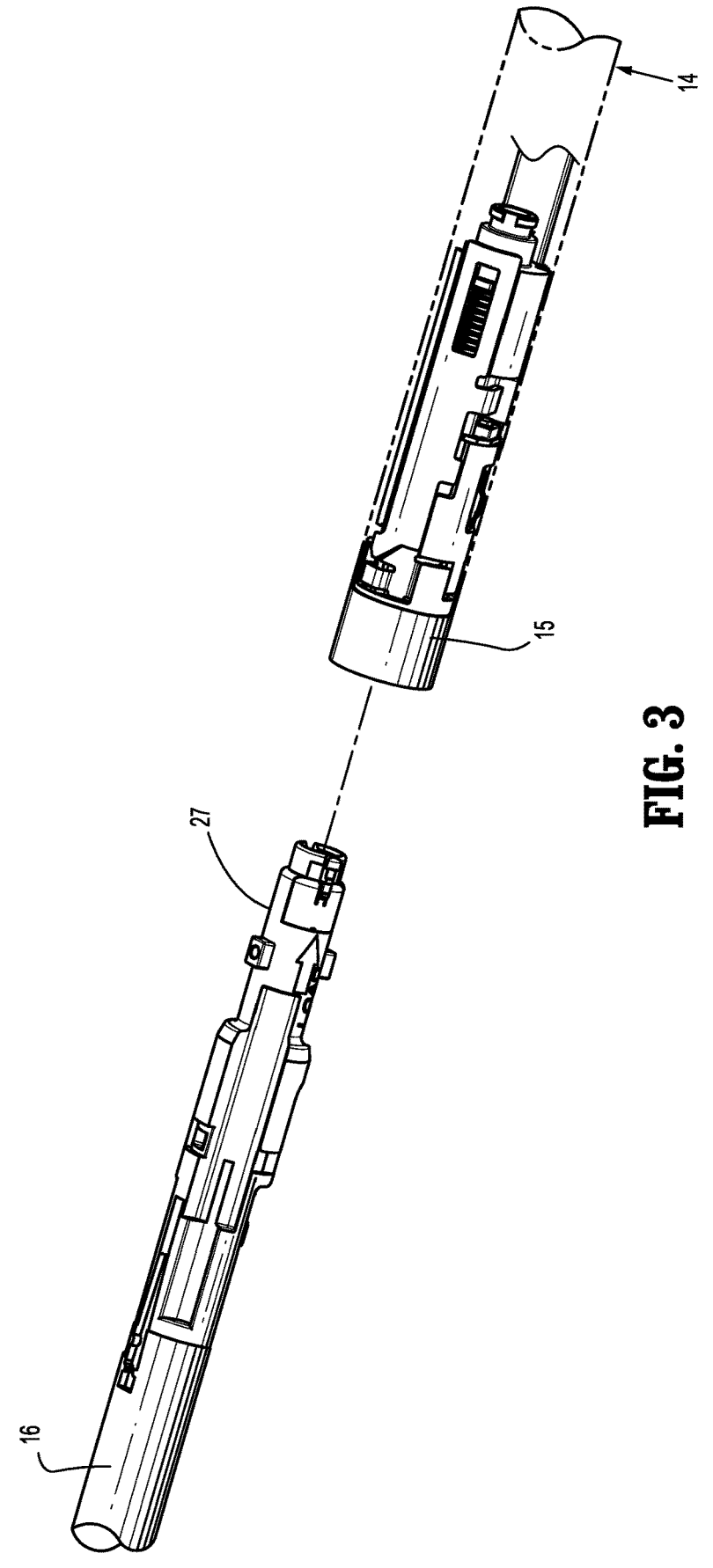
FIG. 3 is a view of a proximal end of a loading unit and a distal end of an adapter assembly of the surgical stapling device shown in FIG. 1.
Figures 4, 5:
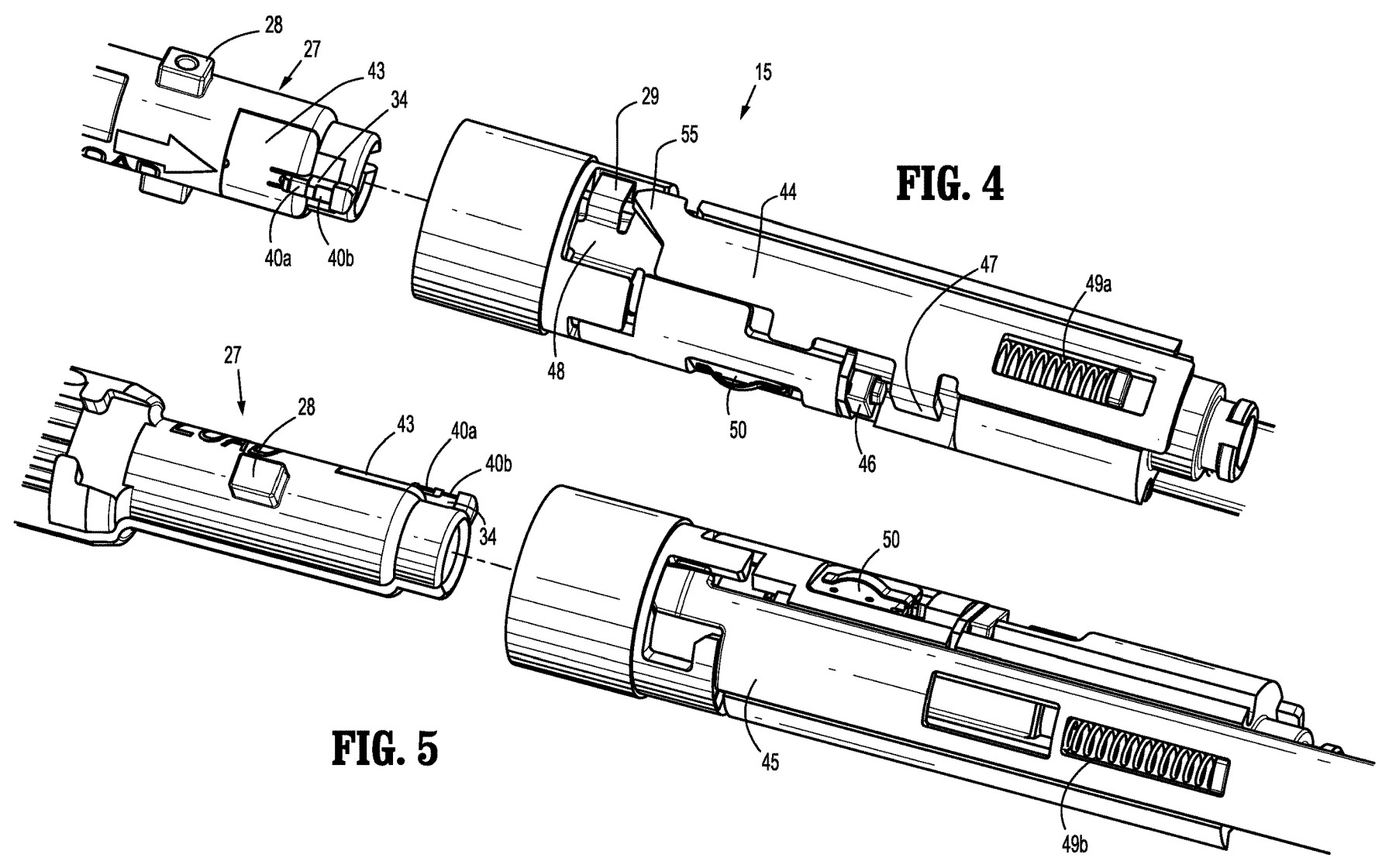

With reference to FIGS. 3, 4, and 5, loading unit coupler 15 of adapter assembly 14 is configured to operably engage adapter coupler 27 of loading unit 16 via a push and twist or bayonet-type arrangement. Adapter coupler 27 includes one or more bayonet lugs 28 that are configured to mate with corresponding one or more bayonet channels 29 defined in a bayonet collar 48 provided by loading unit coupler 15 of adapter assembly 14. A short link member 44 and a load link member 45 are longitudinally disposed within adapter assembly 14 and are configured to translate longitudinally (e.g., distally and proximally) during operation of stapler 10. A cam 55 disposed at a distal end of short link member 44 is urged distally against a bayonet channel 29 by spring 49*a*. To engage loading unit 16 with adapter assembly 14, adapter coupler 27 of loading unit 16 is inserted into loading unit coupler 15 of adapter assembly 14 and rotated. In turn, bayonet collar 48 rotates cooperatively with adapter coupler 27. As bayonet collar 48 rotates, cam 55 rides off bayonet channel 29, causing short link member 44 to translate distally, which, in turn, causes a switch tab 47 formed in short link member 44 to actuate switch 46. Switch 46 is in operative electrical communication with the controller 21*a* and is configured to convey thereto the engagement status between loading unit 16 and adapter assembly 14.

Figure 11:
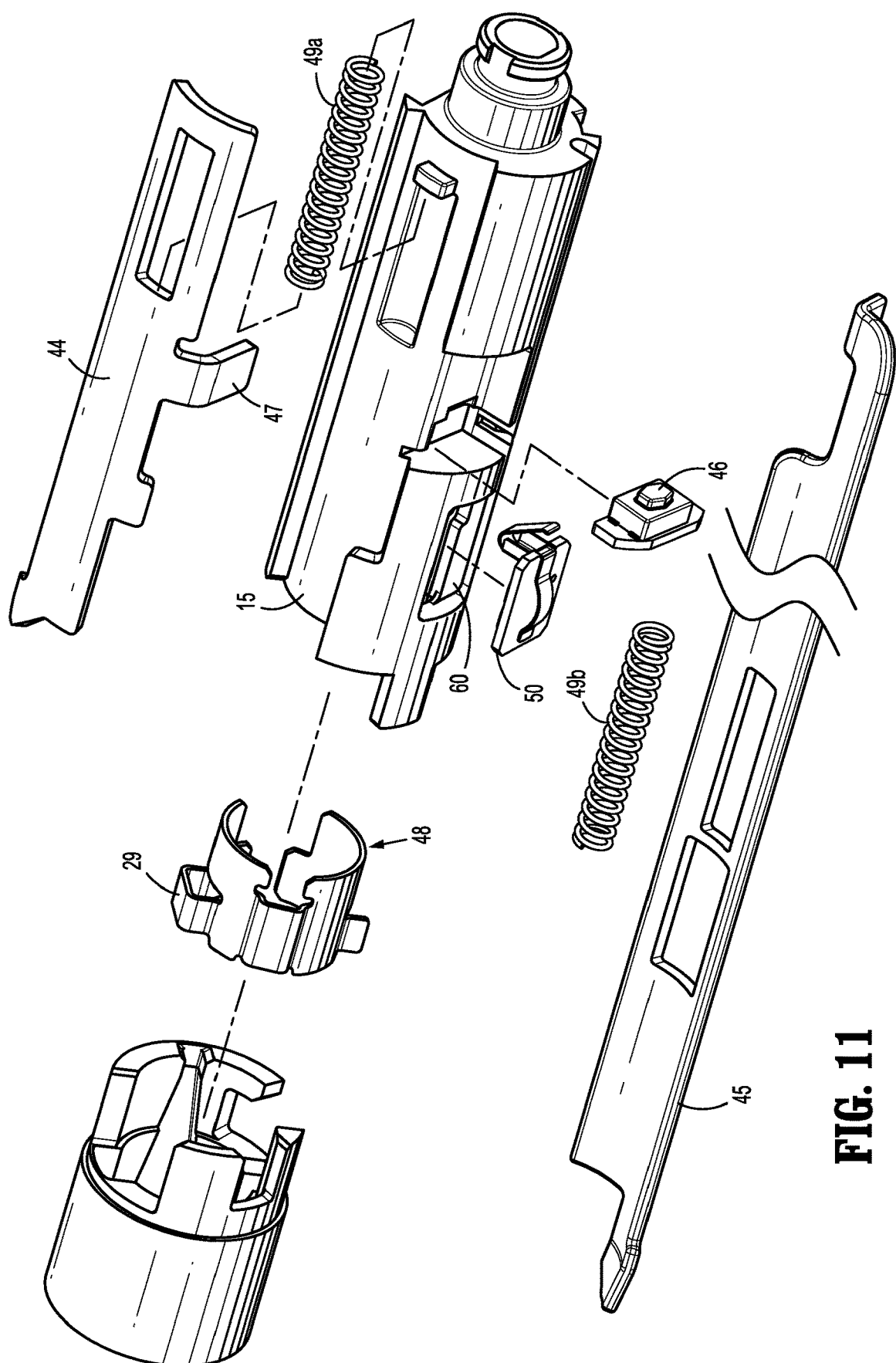
FIG. 11 is an enlarged, exploded view of the distal end of the adapter assembly shown in FIG. 3 with the adapter assembly and adapter board separated.
Figure 12:
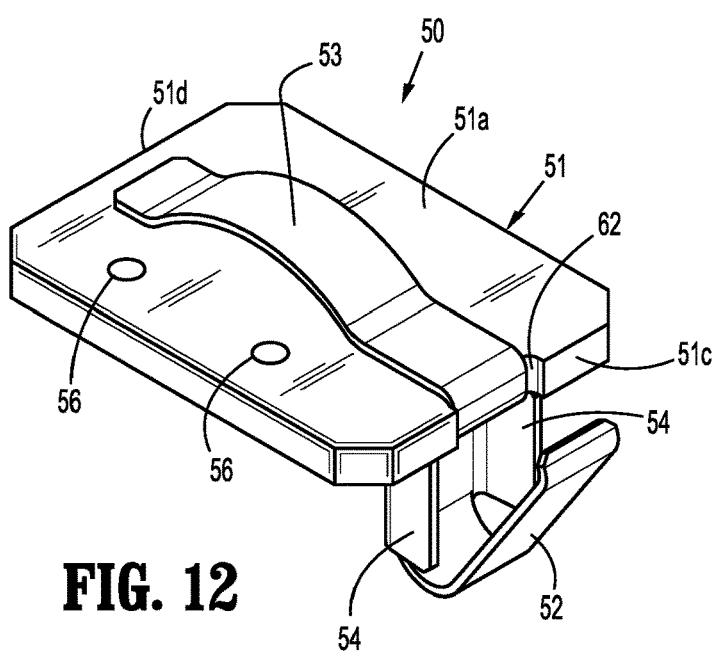
FIG. 12 is an enlarged view of the adapter board shown in FIG. 11.
Figure 13:
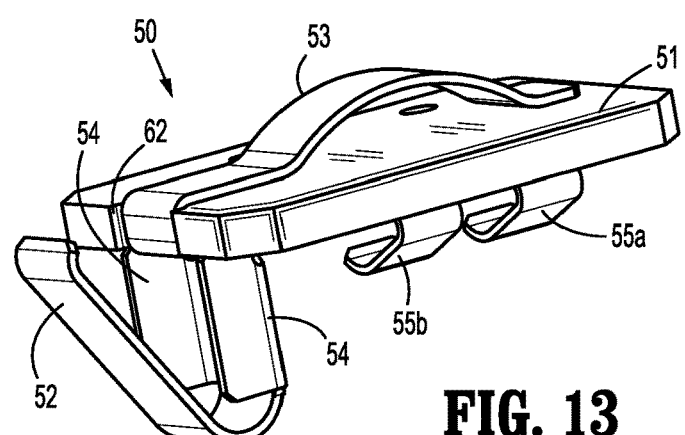
FIG. 13 is another enlarged view of the adapter board shown in FIG. 11.
Figure 14:
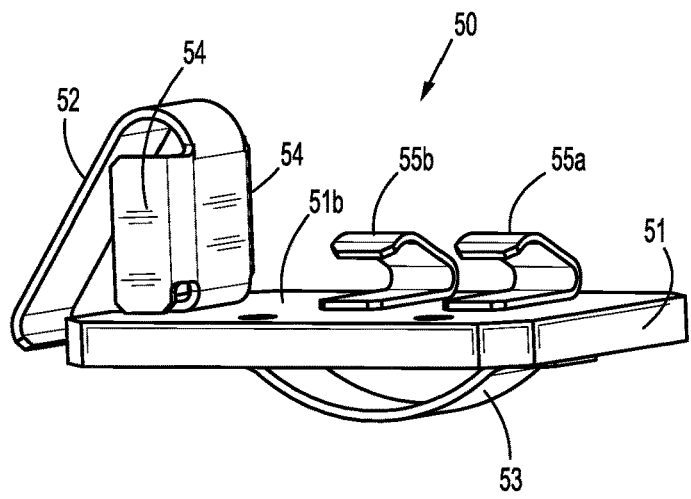
FIG. 14 is yet another enlarged view of the adapter board shown in FIG. 11.

Turning now to FIGS. 6-10, adapter coupler 27 of loading unit 16 includes an authentication board assembly 30 that is configured to be securely mounted within a recess 31 defined in adapter coupler 27. Authentication board assembly 30 is positioned within adapter coupler 27 such that when loading unit 16 is secured to adapter assembly 14, authentication board assembly 30 engages an adapter board assembly 50 mounted within loading unit coupler 15 of the adapter assembly (FIG. 11). In more detail, authentication board 30 includes a circuit board 37, a pair of contact members 40*a, 40*b* (collectively, contact members 40) and a chip 36. Circuit board 37 defines a substantially planar elongated member configured to be securely received within recess 31 defined by adapter coupler 27. Chip 36 is in electrical communication with contact members 40. A distal end 37*a* of circuit board 37 supports chip 36, and a proximal end 37*b* of circuit board 37 supports contact members 40. Distal end 37*a* of circuit board 37 includes an alignment notch 33 defined therein that is configured to engage a corresponding alignment nub 32 provided at a distal end of recess 31 to ensure secure and accurate positioning of authentication board assembly 30 within adapter coupler 27.

Chip 36 includes any chip capable of storing the specifications of loading unit 16, such as, without limitation, cartridge size, staple arrangement, staple length, clamp-up distance, date of manufacture, expiration date, compatibility characteristics, a unique identifier (e.g., a serial number), and/or number of uses, and transmitting the specifications to handle assembly 12. In some embodiments, chip 36 includes an erasable programmable read only memory ("EPROM") chip. In this manner, the handle assembly 12 may adjust the firing forces, firing stroke, and/or other operational characteristics thereof in accordance with the specifications of loading unit 16 that are transmitted from chip 36. It is further envisioned that chip 36 may include write capabilities which allow handle assembly 12 to communicate to chip 36 that the associated loading unit 16 has been used, which can prevent reloading or reuse of an expended reload assembly, or any other unauthorized use.

In some embodiments, chip 36 includes a secure authentication chip, such as, without limitation, a DS28E15 Deep-Cover™ Secure Authenticator with 1-Wire SHA-256 and 512-Bit User EEPROM, manufactured by Maxim Integrated™ of San Jose, California. In these embodiments, the contents of chip 36, and the communications between chip 36 and handle assembly 12, are encrypted to prevent unauthorized access. In this manner, the use of low-quality counterfeit, re-manufactured, or "knock-off" loading units is effectively discouraged, which, in turn, reduces risk to patients by ensuring that only fresh, authentic loading units 16 are used during surgical procedures. In addition, the likelihood that medical facilities and/or surgeons may unwittingly use counterfeit loading units is greatly curtailed, thus reducing the overall costs to society for delivering medical services. In some embodiments, chip 36 utilizes a "1-wire" communications interface whereby a single signal conductor is employed, together with a ground conductor, for bidirectional serial communications between chip 36 and handle assembly 12.

Contact assembly 38 (FIGS. 9, 10) includes a short contact arm 41 and a long contact arm 42 joined by a contact base 59, and having a generally elongated u-shaped configuration. Short contact arm 41 includes a first contact member 40*a* orthogonally disposed and fixed to an upper portion of a proximal end thereof. Long contact arm 42 includes a second contact member 40*b* orthogonally disposed and fixed to an upper portion of a proximal end thereof. Short and long contact arms 41, 42 each include a solder tab 39 orthogonally disposed and fixed to a lower portion of a distal end thereof. Solder tabs 39 are electromechanically joined to a proximal end 37*b* of circuit board 37 by, e.g., soldering, electrically conductive adhesive, and/or other suitable technique.

Figures 6, 7:
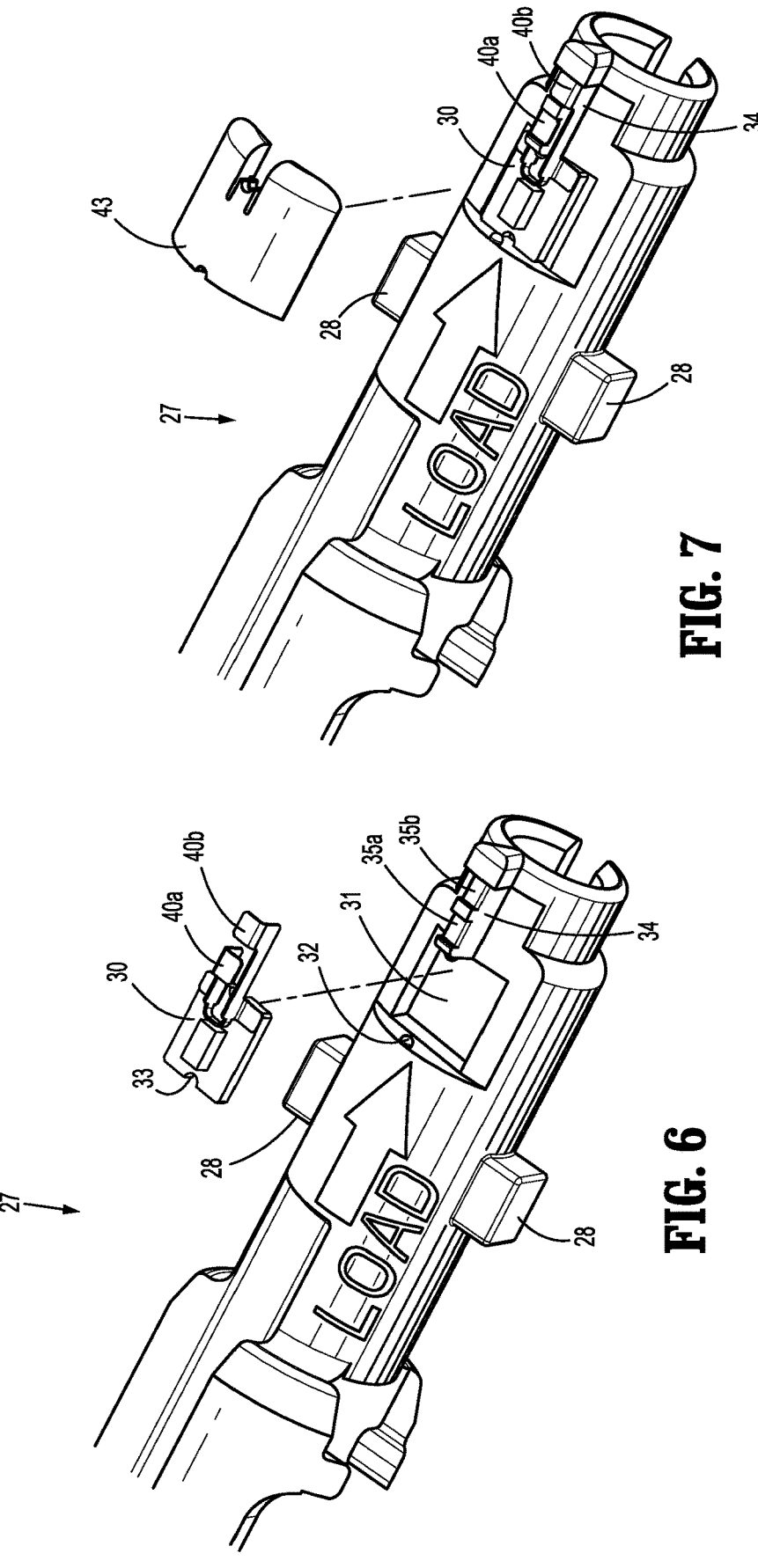
FIG. 6 is an enlarged, exploded view of the proximal end of the loading unit shown in FIG. 3 with the loading unit and authentication board separated.
FIG. 7 is an enlarged, partially-exploded view of the proximal end of the loading unit shown in FIG. 3 with the authentication board cover separated from the loading unit.
Figures 8, 9, 10:
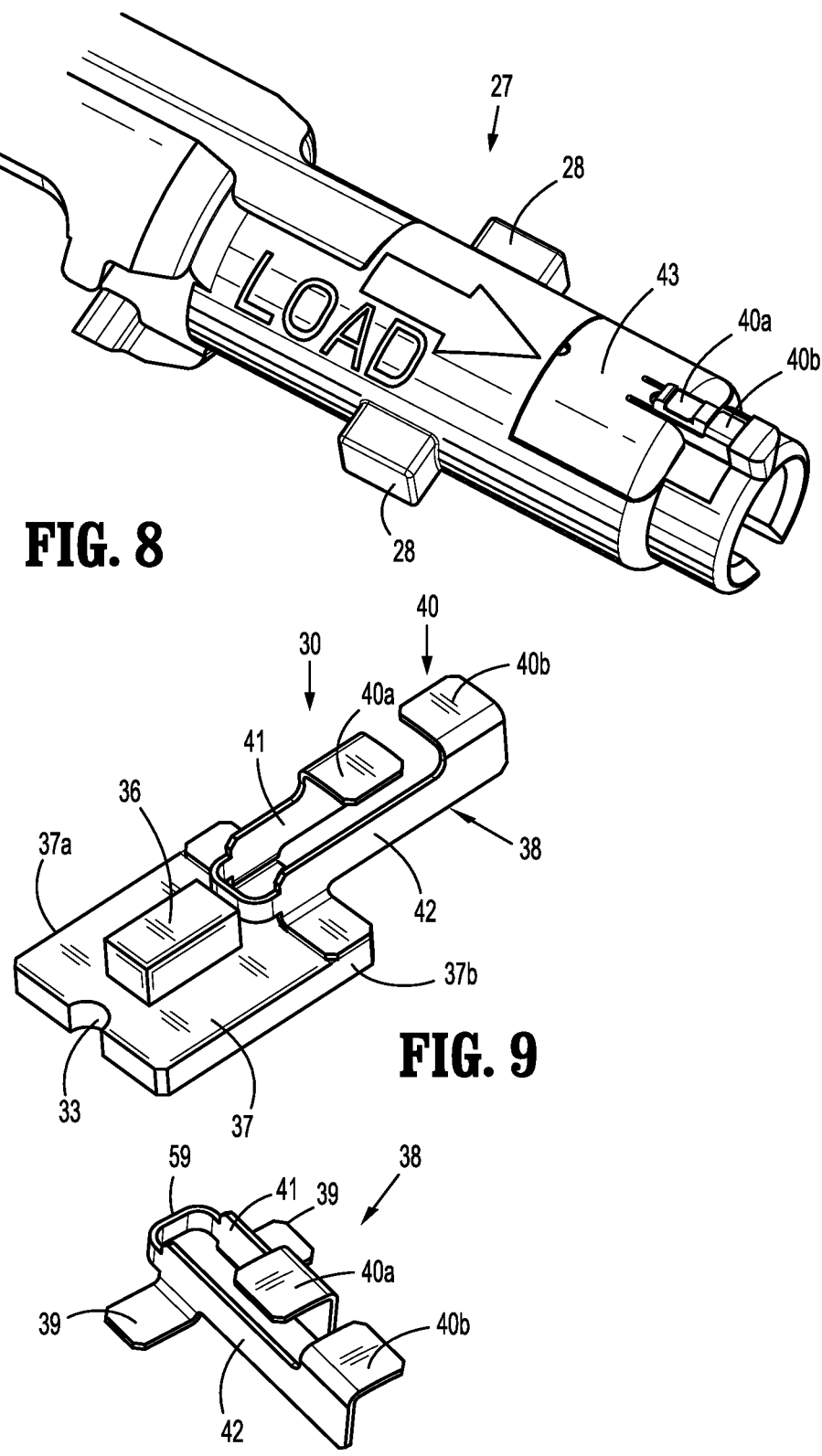
FIG. 8 is an enlarged view of the proximal end of the loading unit shown in FIG. 3.
FIG. 9 is a perspective view of an authentication board assembly according to an embodiment of the present disclosure.
FIG. 10 is a perspective view of an authentication board contact.

Adapter coupler 27 includes a raised contact support 34 extending radially from a proximal end thereof and includes a pair of cradles 35a, 35b defined therein that are configured to receive first contact member 40a and second contact member 40b, respectively, when authentication board assembly 30 is positioned within recess 31 of adapter coupler 27. A cover 43 is configured to enclose and retain authentication board assembly 30 within recess 31 of adapter coupler 27 (FIGS. 7 and 8).

In some embodiments, short contact arm 41 and first contact member 40a are electrically insulated from long contact arm 42 and second contact member 40b by contact base 59. In these embodiments, each of short contact arm 41 and long contact arm 42 carries a separate circuit, e.g., short contact arm 41 carries signal and long contact arm 42 carries ground. In other embodiments, short contact arm 41 and first contact member 40a are electrically joined with long contact arm 42 and second contact member 40b. In these embodiments, short contact arm 41 and long contact arm 42 operate in a bifurcated or redundant mode to carry a signal circuit, while the ground circuit is carried through other electrically conductive components of loading unit 16, adapter unit 14, and/or handle assembly 12.

As mentioned above, authentication board assembly 30 is configured to engage adapter board assembly 50 mounted within loading unit coupler 15 when loading unit 16 is secured to adapter assembly 14. With reference now to FIGS. 11-14, loading unit coupler 15 includes an adapter board assembly 50 that is configured to be floatingly mounted within a pocket 60 defined in loading unit coupler 15. Adapter board assembly 50 is positioned within loading unit coupler 15 such that when loading unit 16 is secured to adapter assembly 14, adapter board assembly 50 engages authentication board assembly 30.

Adapter board assembly 50 includes a circuit board 51 having a pair of contact members 55a, 55b (collectively, contact members 55) fixed thereto and in operable communication with handle assembly 12. In the illustrated embodiment, contact members 55a, 55b are arranged for effective engagement in a transverse direction, e.g., transverse to the longitudinal axis "X-X" of stapler 10, to accommodate the rotational coupling of loading unit 16 and adapter assembly 14 as described herein.

Circuit board 51 includes an upper surface 51a, a lower surface 51b, a proximal end 51c, and a distal end 51d. Circuit board 51 defines a substantially planar elongated member configured to be resiliently or floatingly received within pocket 60 defined by loading unit coupler 15. A spring clip 52 is fixed to a proximal end 51c of circuit board 51 and is configured to support adapter board assembly 50 within pocket 60. Spring clip 52 includes a pair of spring supports 54 having a wing-like configuration that are configured prevent spring clip 52 from over-extension and to provide stiffness thereto. Adapter board assembly 50 includes a spring 53 having a broad, curvate u-shaped profile disposed on an upper surface 51a of circuit board 51. In some embodiments, spring clip 52 and spring 53 may be integrally formed. Spring clip 52 and/or spring 53 may be positively aligned and/or supported by a notch 62 defined in proximal end 51c of circuit board 51. Circuit board 51 includes one or more through holes 56 defined therein that may be utilized to form a conductive pathway between upper surface 51a and lower surface 51b of circuit board 51.

Figures 15, 16:
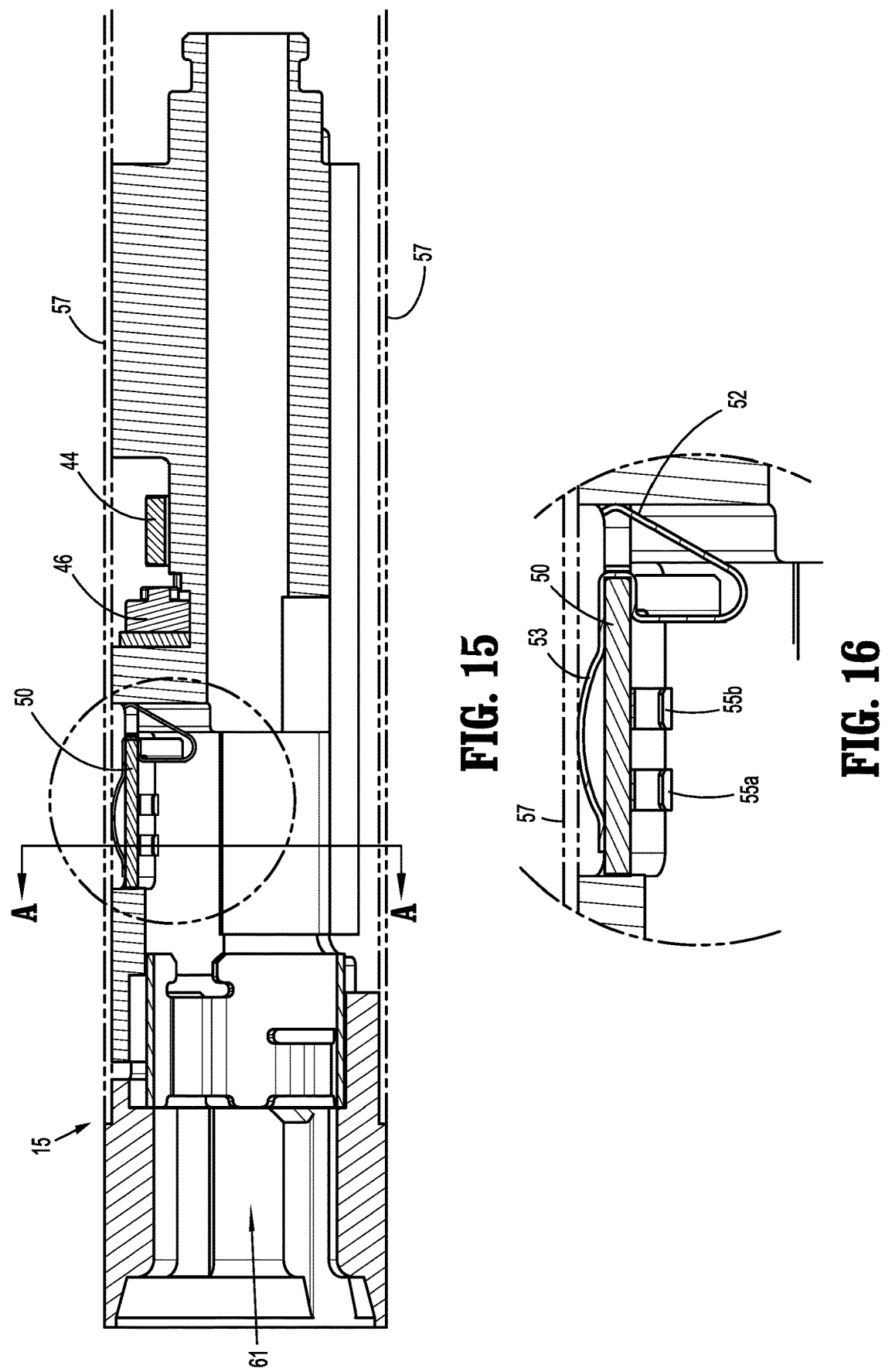
FIG. 15 is a cross-sectional, side view of the adapter assembly shown in FIG. 3 showing the adapter assembly separated from the loading unit.
FIG. 16 is an enlarged view of the indicated area shown in FIG. 15 showing the adapter board separated from the authentication board.
Figures 17, 18:
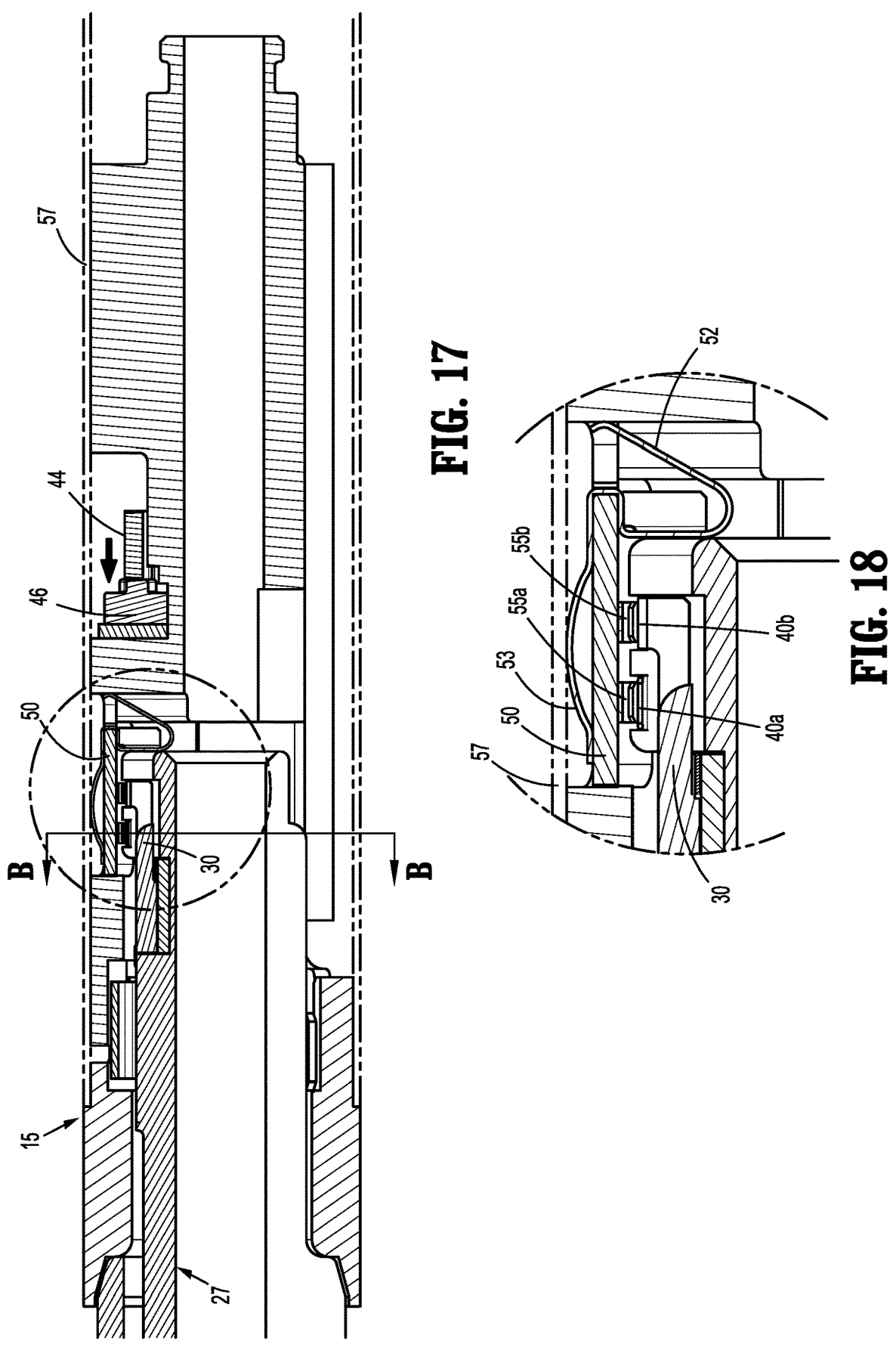
FIG. 17 is a cross-sectional, side view of the adapter assembly shown in FIG. 3 showing the adapter assembly engaged with the loading unit.
FIG. 18 is an enlarged view of the indicated area shown in FIG. 17 showing the adapter board engaged with the authentication board.

When adapter board assembly 50 is mounted within pocket 60, spring 53 bears against outer tube 57 of adapter assembly 14 (FIGS. 15, 16). In use, adapter board assembly 50 is spring-biased towards authentication board assembly 30 by spring 53 and by side spring clip 52 such that, upon joining loading unit 16 and adapter assembly 14, any manufacturing tolerances between loading unit 16 and adapter assembly 14 are compensated for by engagement of the floating spring mount of adapter board assembly 50 within pocket 60. In this manner, a reliable connection between contact members 55 of adapter board assembly 50 and contact members 40 of authentication board assembly 30 is consistently achieved, thus providing a robust communication link between chip 36 and handle assembly 12. In embodiments, contact assembly 38, contacts 40, and/or contacts 55 are formed at least in part from electrically conductive material, such as, without limitation, beryllium copper.

Figures 19, 20, 21:
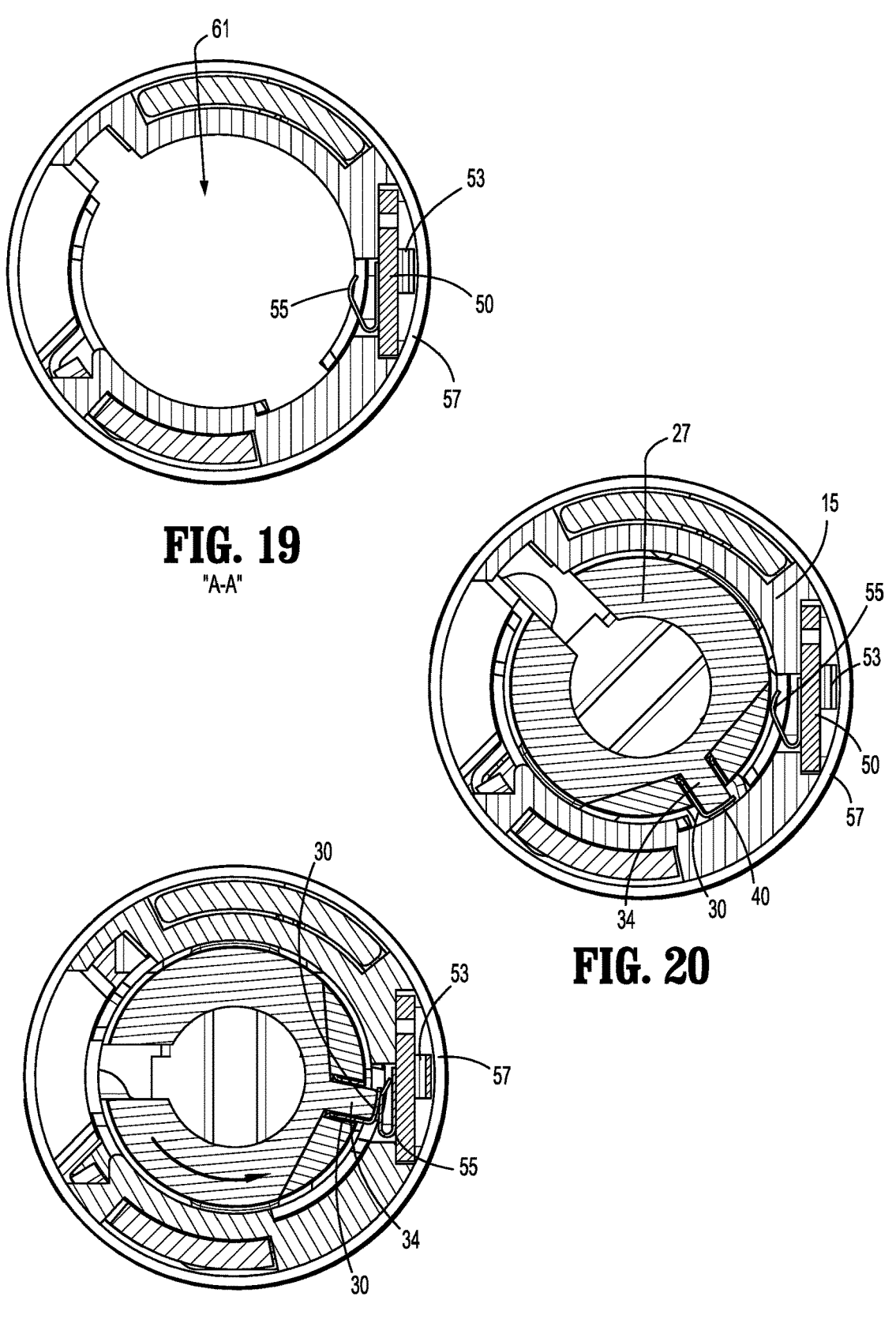
FIG. 19 is a cross-sectional, axial view of the adapter assembly shown in FIG. 3 showing the adapter assembly separated from the loading unit.
FIG. 20 is a cross-sectional, axial view of the adapter assembly shown in FIG. 3 showing the loading unit inserted into the adapter assembly.
FIG. 21 is a cross-sectional, axial view of the adapter assembly shown in FIG. 3 showing the loading unit engaged with the adapter assembly.
Figure 22:
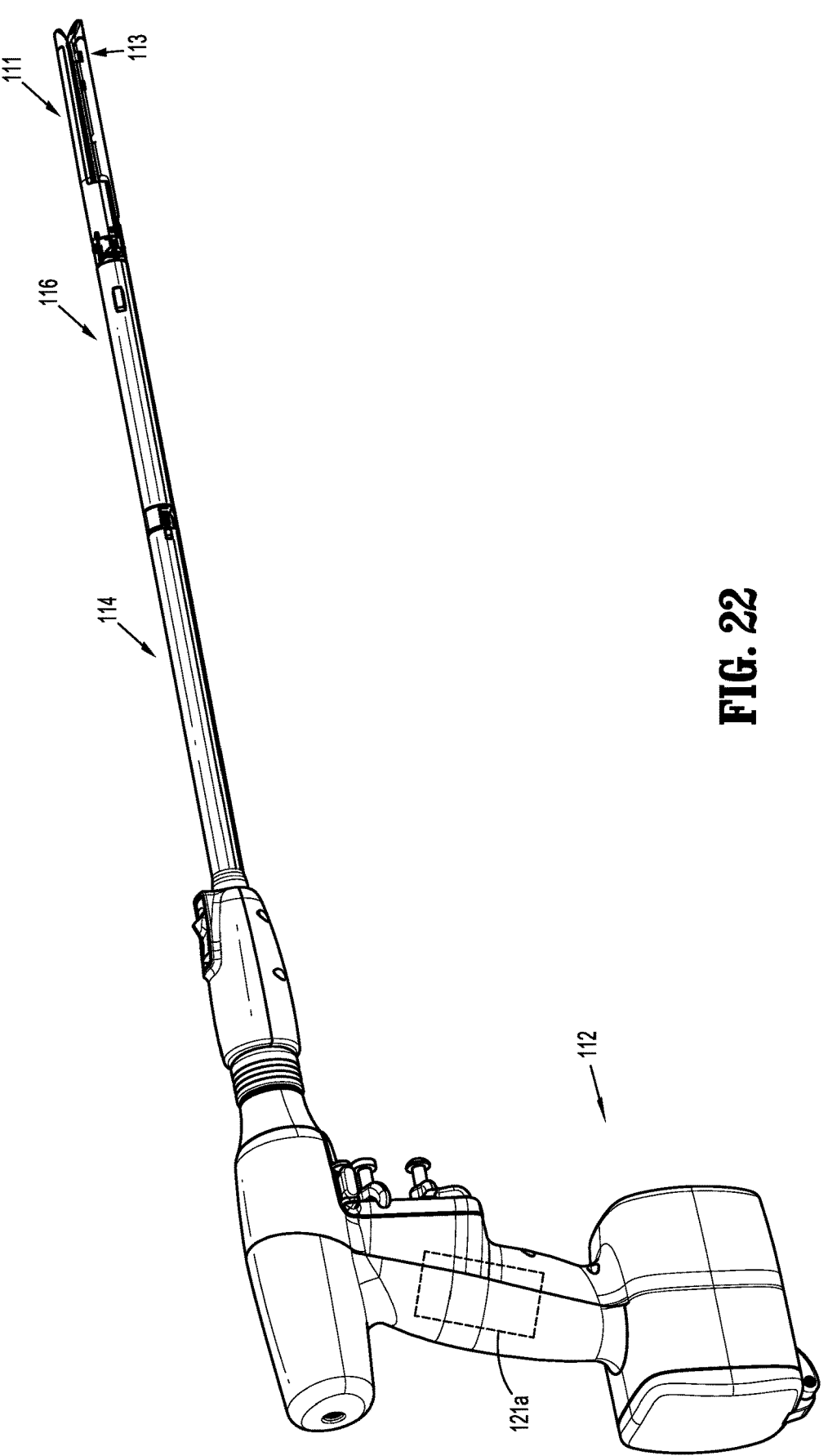
FIG. 22 is a perspective view of a surgical stapling device according to further embodiments of the present disclosure.
Figure 23:
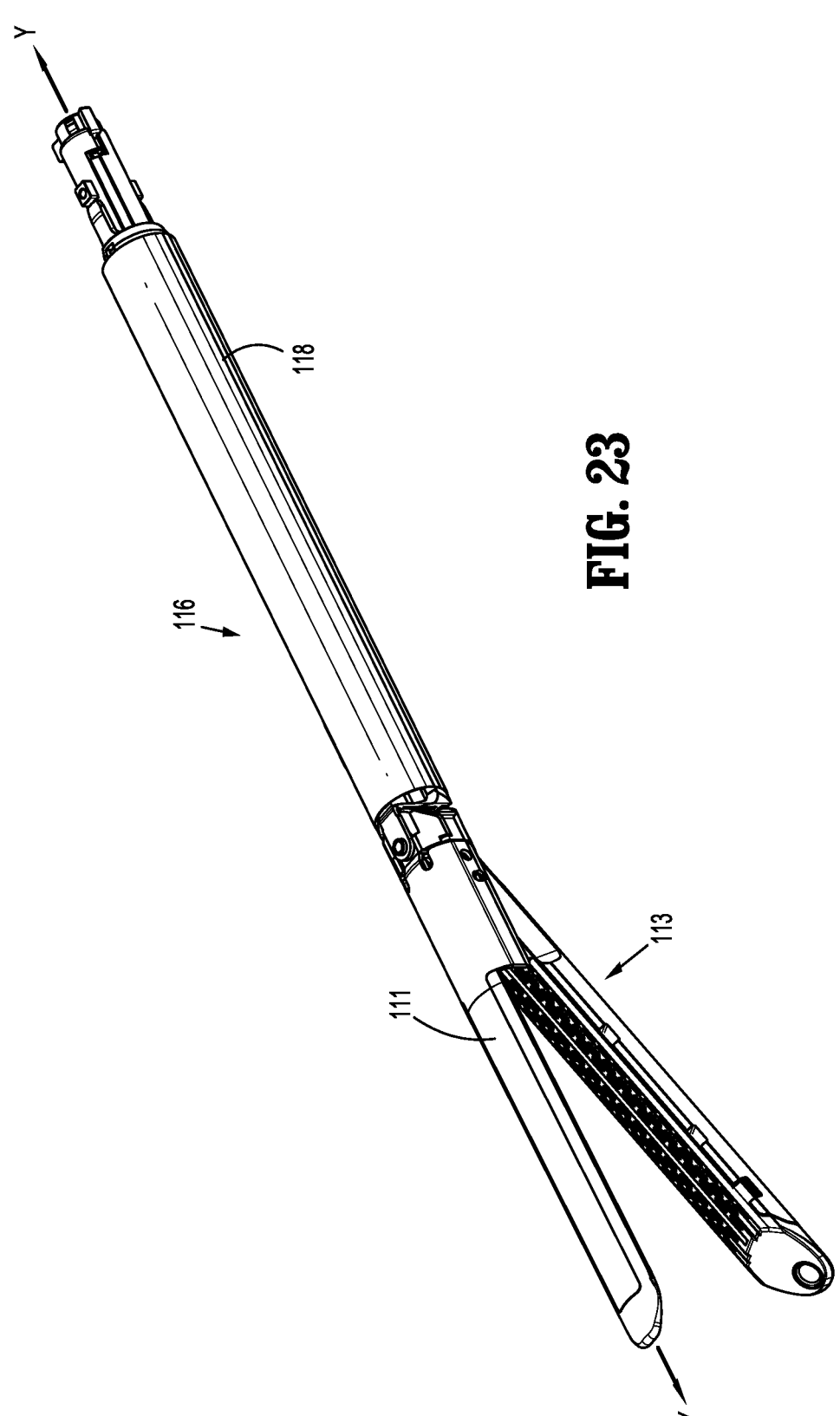
FIG. 23 is a perspective view of a loading unit according to embodiments of the present disclosure.
Figure 24:
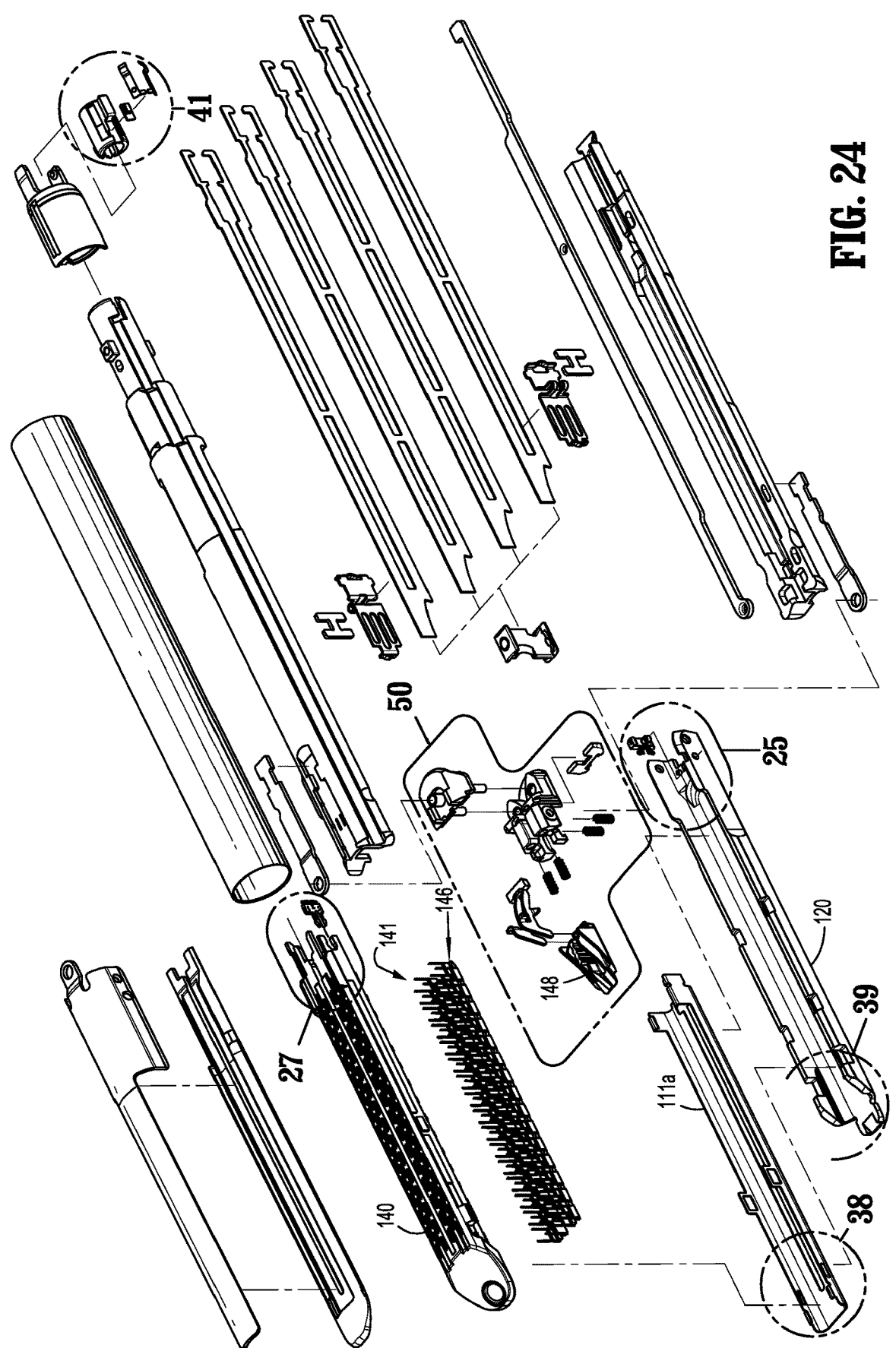
FIG. 24 is the loading unit of FIG. 23 shown with parts separated.
Figures 25, 26:
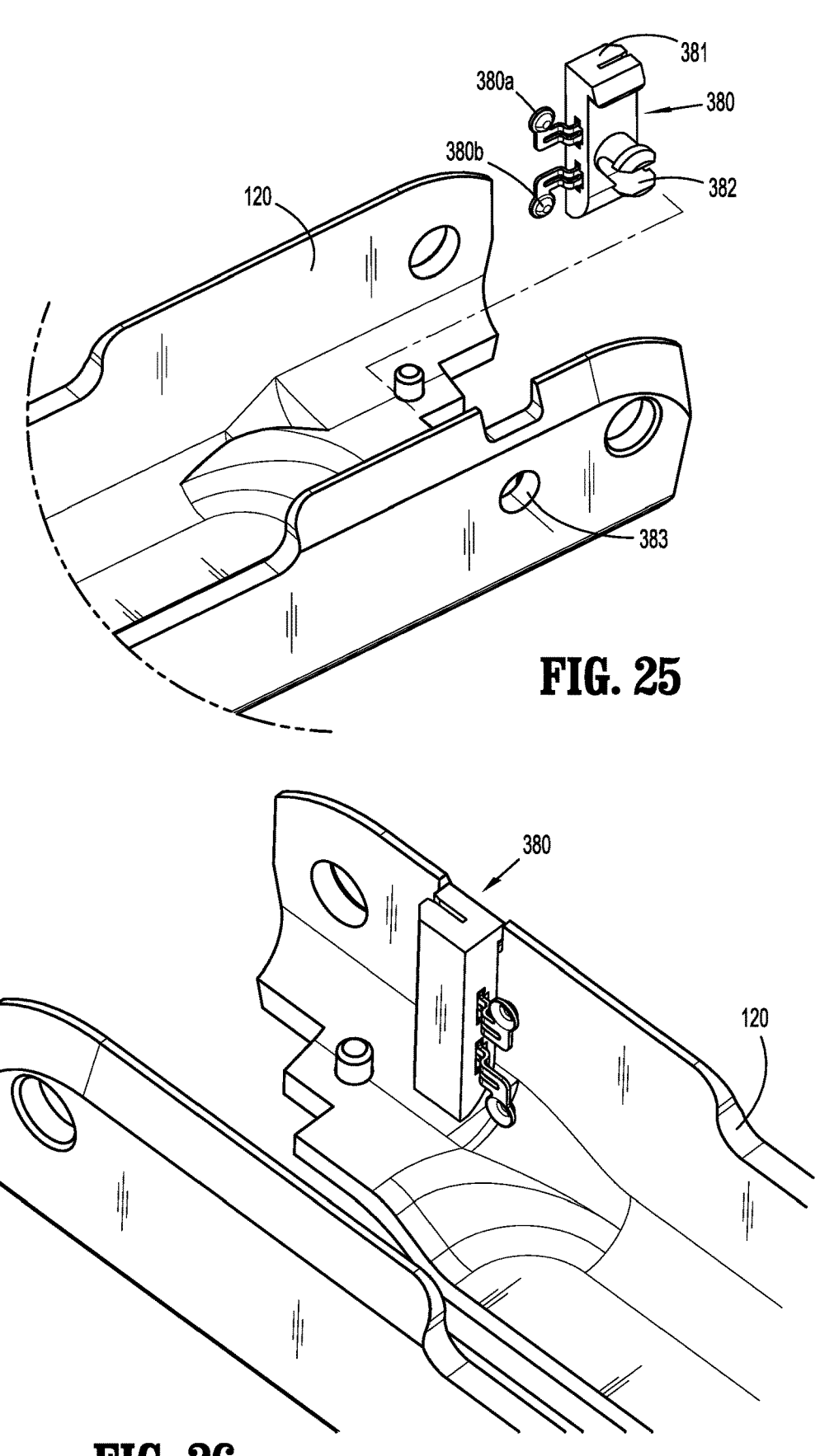
FIG. 25 is a detailed perspective view of a board assembly.
FIG. 26 is a another detailed perspective view of the board assembly of FIG. 25.

Turning now to FIGS. 15-21, the interaction between adapter board assembly 50 and authentication board assembly 30 is shown. As seen in FIGS. 15, 16, and 19, adapter board assembly 50 is retained within loading unit adapter 15 by spring clip 52. Spring 53 bears against outer tube 57 to bias adapter board assembly 50 inwardly towards bore 61, such that contact members 55 extend into bore 61. As adapter coupler 27 is inserted fully into bore 61 of loading unit adapter 15, the initial rotational orientation of adapter coupler 27 and loading unit coupler 15 is such that contact members 40 of authentication board 30 and contact members 55 of adapter board assembly 50 are roughly 45° apart (FIG. 20). As loading unit 16 is rotated with respect to adapter assembly 14, contact members 40 of authentication board 30 are brought into engagement with contact members 55 of adapter board assembly 50. Advantageously, contact support 34 of adapter coupler 27 of loading unit 16 provides radial support to contact members 30 as they engage mating contact members 55 of adapter board assembly 50. In addition, spring 53 bears against outer tube 57 which enables adapter board assembly 50 to float with respect to authentication board 30 and loading unit coupler 15, thereby compensating for manufacturing variations between the various components and providing a reliable connection between authentication board 30 and adapter board assembly 50.

It is contemplated that a loading unit like loading unit 16 could have a removable and replaceable staple cartridge assembly. A stapling system is shown in FIGS. 22-57, in accordance with an embodiment of the present disclosure, having a powered handle assembly 112 similar to the handle assembly 12 discussed above. The handle assembly is configured as discussed above and has a controller 121a. The stapling system includes an adapter assembly 114 and a loading unit 116, each of which can be configured as discussed above. The loading unit is a linear stapling loading unit, but other types of loading units are contemplated. The loading unit 116 has a drive assembly for firing staples into tissue clamped between the anvil jaw member 111 and staple cartridge jaw member 113, as discussed above.

Supported in the staple cartridge jaw member 113 is a removable and replaceable staple cartridge assembly 115. A removable and replaceable staple cartridge assembly is disclosed in U.S. patent application Ser. No. 13/280,880, filed Oct. 25, 2011, and published as US 2013-0098965 A1, the entire disclosure of which is hereby incorporated by reference herein.

Loading unit 116 of the present disclosure is configured to be used more than once. In particular, the loading unit has the removable staple cartridge assembly 115 that includes the staple cartridge and drive assembly discussed above. The removable assembly 116 is configured to be removed and replaced (e.g., after firing staples or other surgical fasteners therefrom). The loading unit 116 shown includes a proximal body portion 118 that is attachable to the adapter assembly 114. However, the features of the loading units of the present disclosure can be incorporated in a surgical instrument in which does not include a detachable portion of the elongated portion of the instrument.

Loading unit 500 includes a proximal body portion 118 defining a longitudinal axis "A-A". Jaw members include an anvil jaw member 111 and a cartridge jaw member 113. One of the jaw members is pivotal in relation to the other to enable the clamping of tissue between the jaw members. In the illustrated embodiments, the cartridge jaw member 113 is pivotal in relation to the anvil jaw member and is movable between an open or unclamped position and a closed or approximated position. However, the anvil jaw member, or both the cartridge and anvil jaw member, can be movable. As discussed in connection with FIGS. 1-21, the anvil jaw member includes an anvil having a plurality of staple forming depressions.

The cartridge jaw member 113 includes a channel or carrier 120 which receives and supports the staple cartridge assembly 115. The cartridge assembly has a cartridge body 140 and a support plate 111. The cartridge body and support plate are attached to the channel or carrier 120 by a snap-fit connection, as discussed below, a detent, latch, or by another type of connection. The cartridge assembly includes fasteners or staples 141. Cartridge body 140 defines a plurality of laterally spaced staple retention slots 142, which are configured as openings (see FIG. 32). Each slot is configured to receive a fastener or staple therein. Cartridge assembly also defines a plurality of cam wedge slots which accommodate staple pushers 146 and which are open on the bottom to allow the actuation sled 148 to pass longitudinally therethrough in the firing of the staples as discussed above.

The removable staple cartridge assembly 115 includes cartridge body 140 and support plate 111. The removable assembly 115 is removable from channel 120, e.g., after staples have been fired from the cartridge body 140. Another removable and replaceable staple cartridge assembly is capable of being loaded into the channel, such that the loading unit 116 can be actuated again to fire additional fasteners or staples.

Channel 120 includes one or a pair of engagement structures 120a (such as slots) for engaging the staple cartridge assembly and support plate (see FIG. 39), a central slot for the passage of the drive beam, a pair of proximal holes 150 for connection with the anvil jaw member, and a ramped surface 152. Proximal holes 150 are configured to align with/mechanically engage a pair of corresponding holes or features on the anvil jaw member. The jaw members can be connected by pins, for example, to facilitate a pivotal relationship between anvil jaw member 111 and cartridge jaw member 113.

Figure 32:
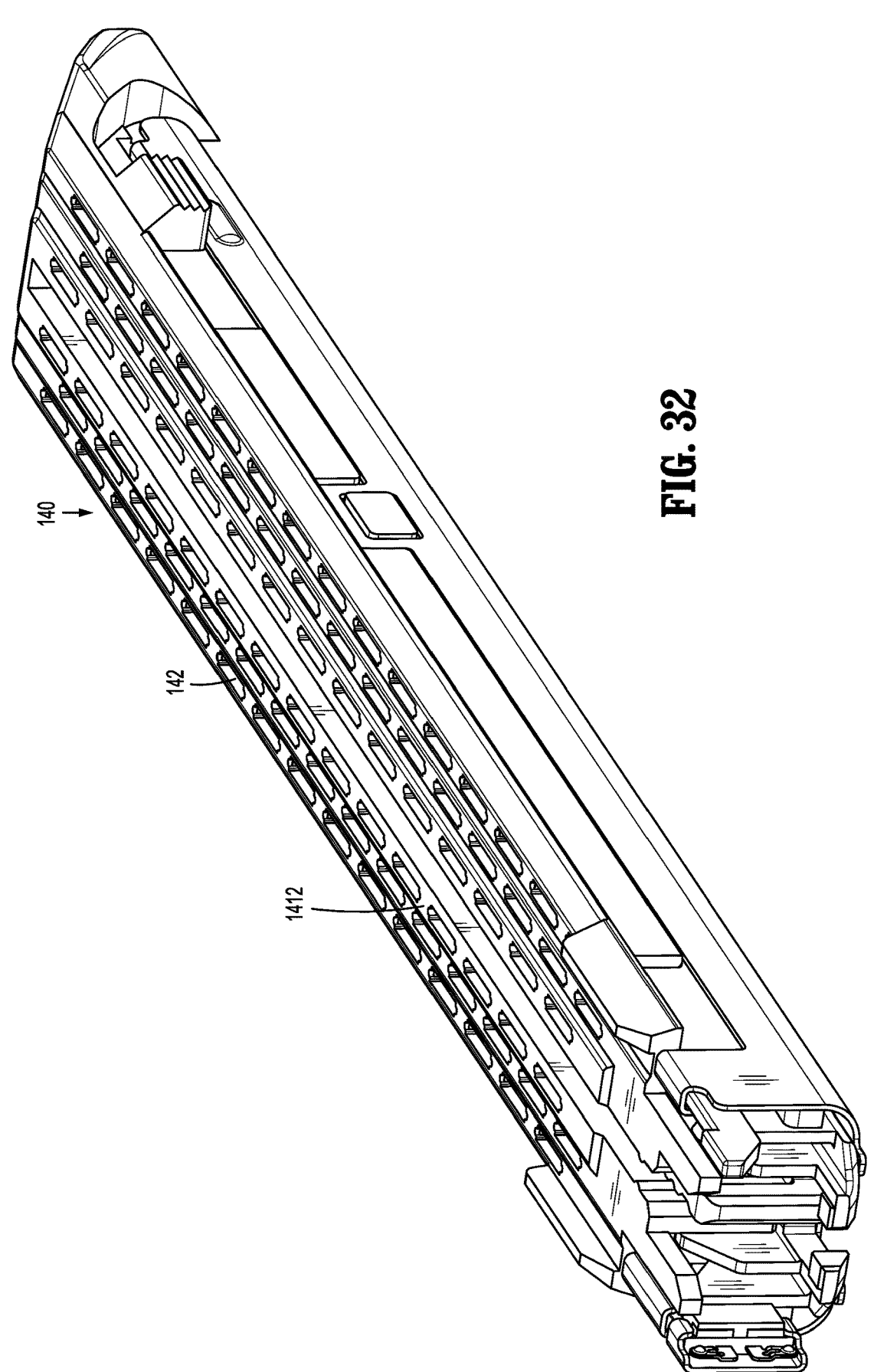
FIG. 32 is a top perspective view of a staple cartridge assembly in accordance with embodiments of the present disclosure.
Figures 33, 34:
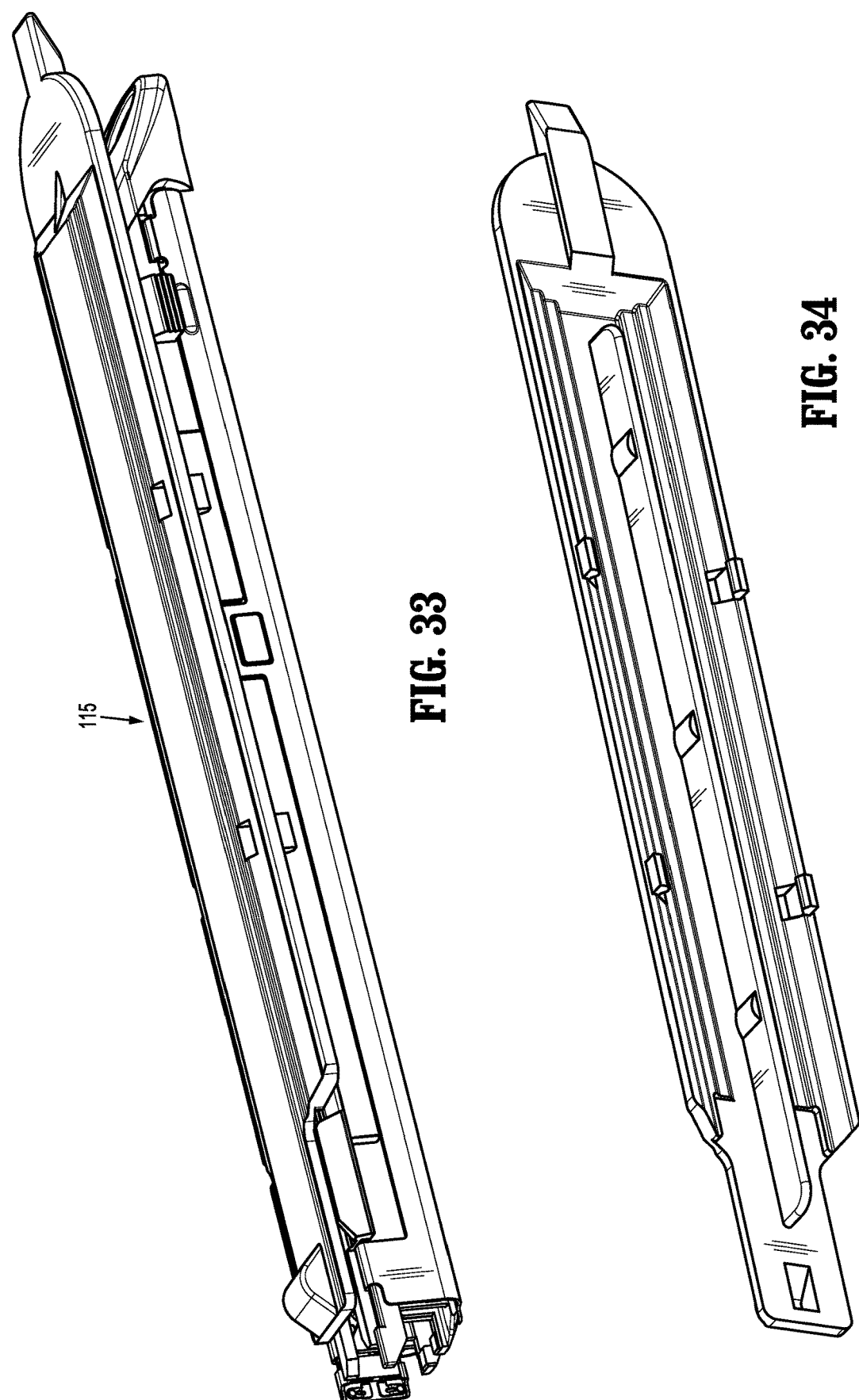
FIG. 33 is a top perspective view of the staple cartridge assembly of FIG. 32, with a shipping wedge.
FIG. 34 is a bottom perspective view of the shipping wedge of FIG. 33.
Figures 35, 36, 37:
FIG. 35 is a detailed perspective view of a lockout assembly in accordance with embodiments of the present disclosure.
FIG. 36 is a perspective view of the loading unit of FIG. 23 showing the staple cartridge assembly.
FIG. 37 is a top view of the loading unit with the anvil and shipping wedge removed.
Figure 38:
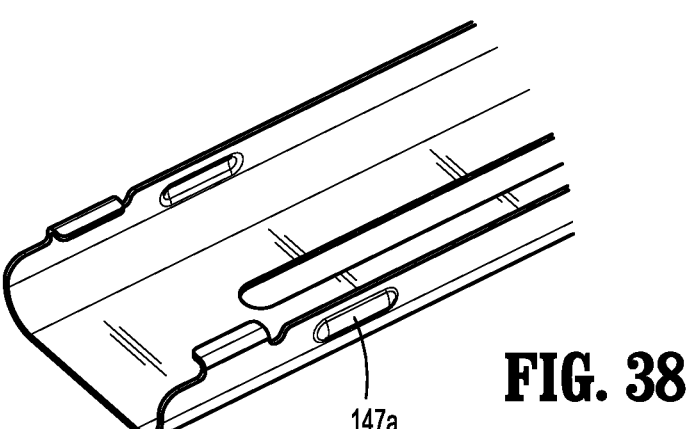
FIG. 38 is a perspective view of the proximal portion of a support plate of the staple cartridge assembly.
Figure 39:
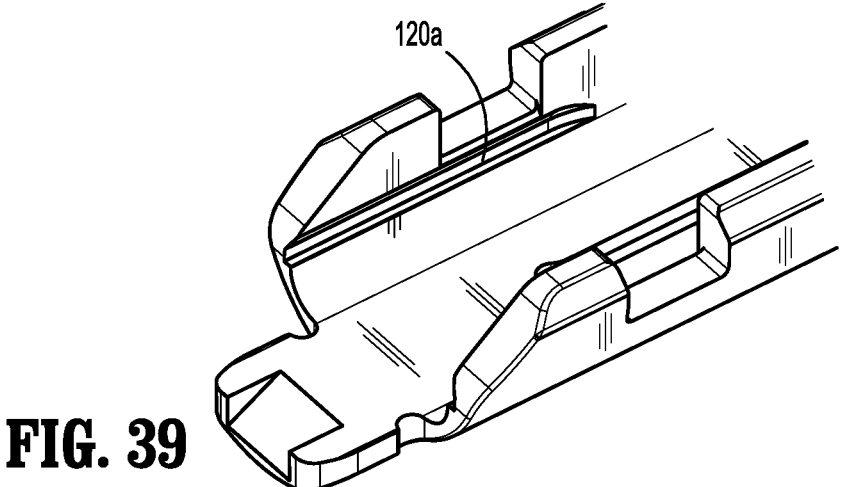
FIG. 39 is a perspective view of the proximal portion of a channel of the loading unit.
Figure 40:
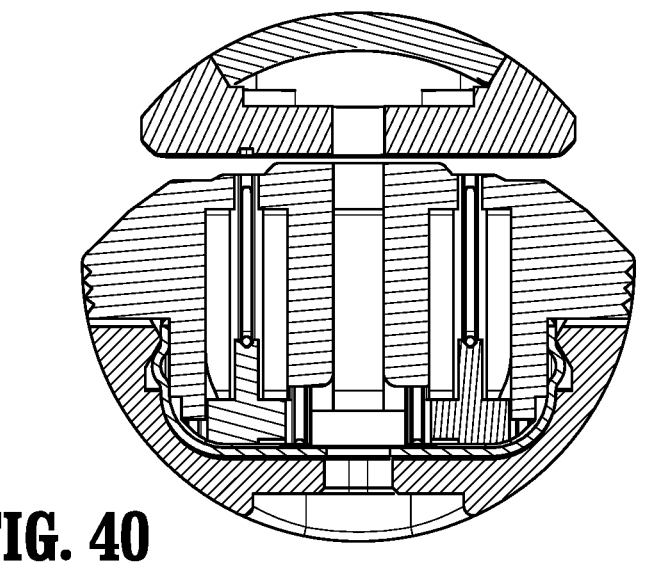
FIG. 40 is a cross sectional view of the loading unit.
Figure 41:
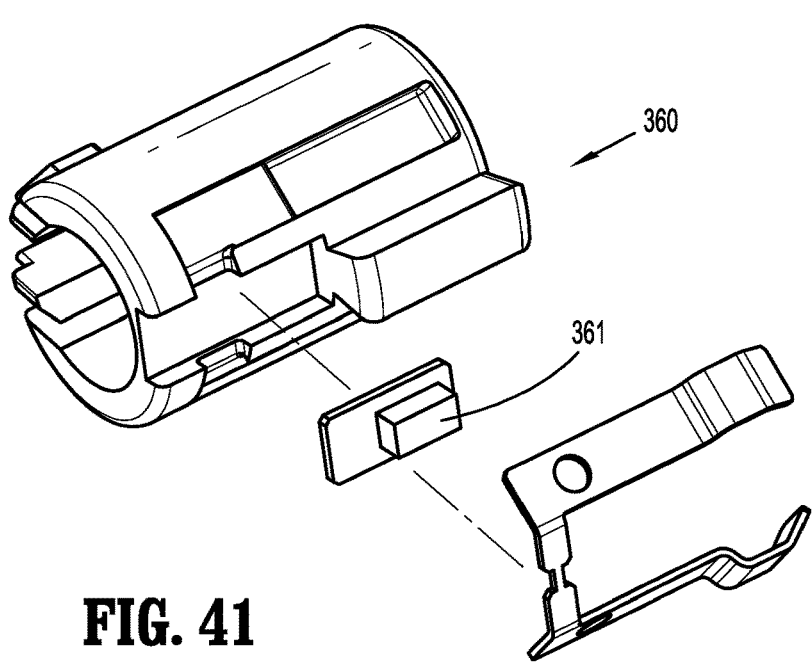
FIG. 41 is a perspective view of a chip assembly of the loading unit with parts separated.
Figure 42:
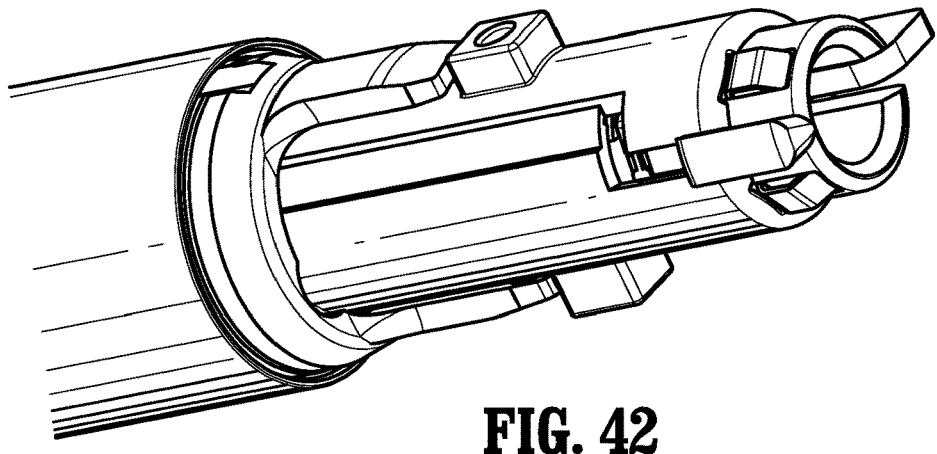
FIG. 42 is a perspective view of the proximal portion of the loading unit.
Figure 43:
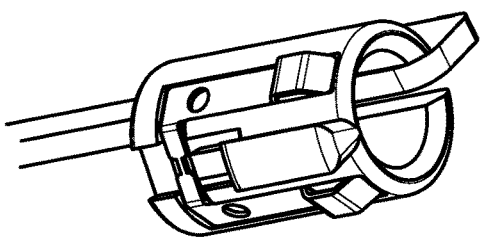
FIG. 43 is a perspective view of the chip assembly.
Figure 47:
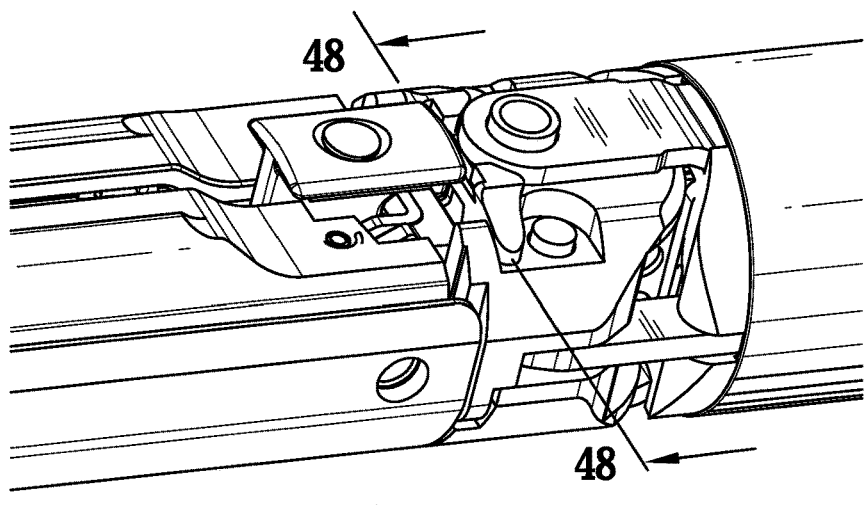
FIG. 47 is another detailed perspective view of a lockout mechanism in accordance with embodiments of the present disclosure.
Figure 48:
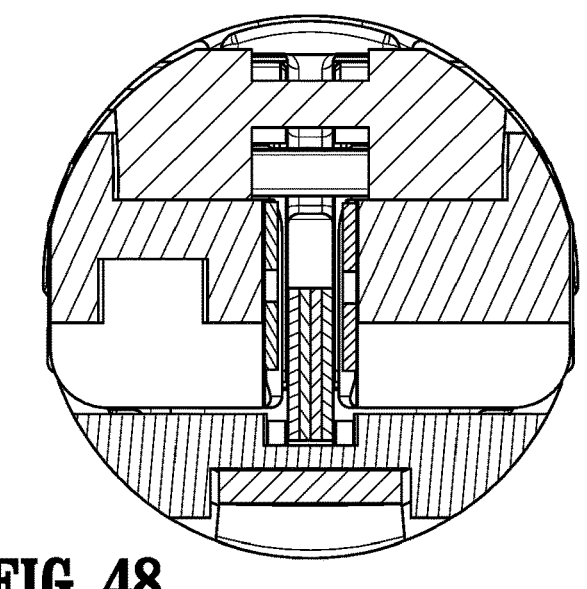
FIG. 48 is a cross sectional view through the drive beam.
Figure 49:
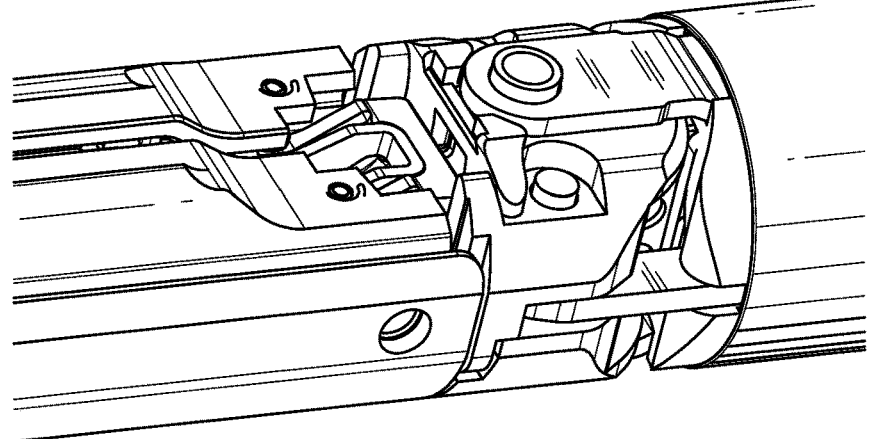
FIG. 49 is a another detailed perspective view of the lockout mechanism.
Figure 50:
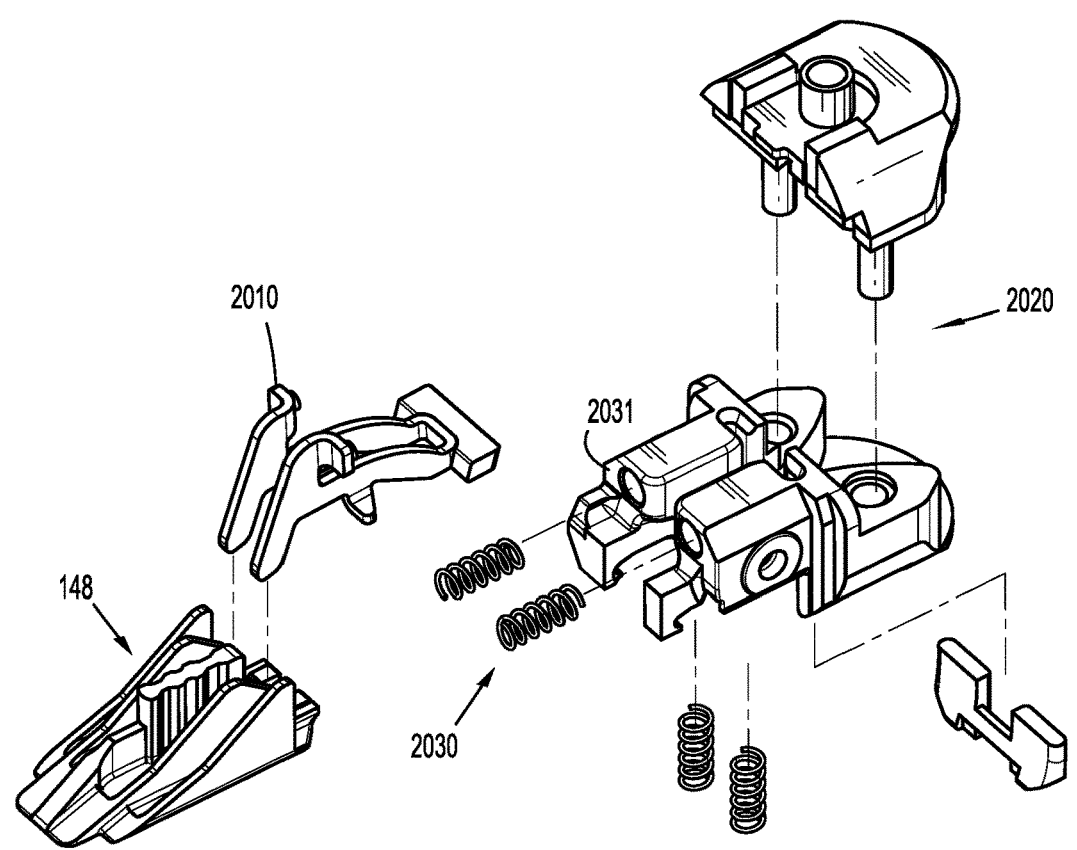
FIG. 50 is a perspective view with parts separated showing a latch, sled, and mounting portion.
Figure 51:
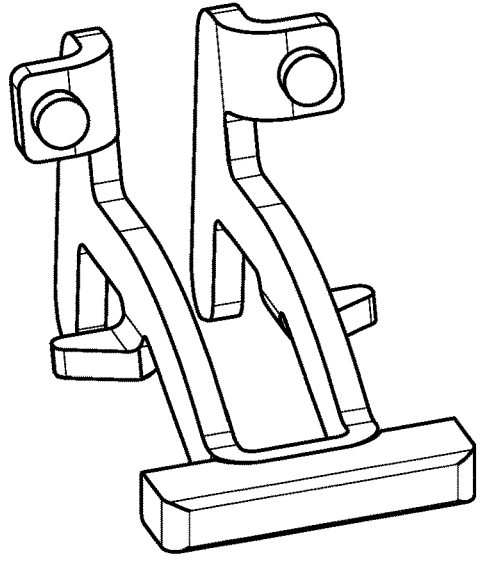
FIG. 51 is a perspective view of the latch.
Figure 52:
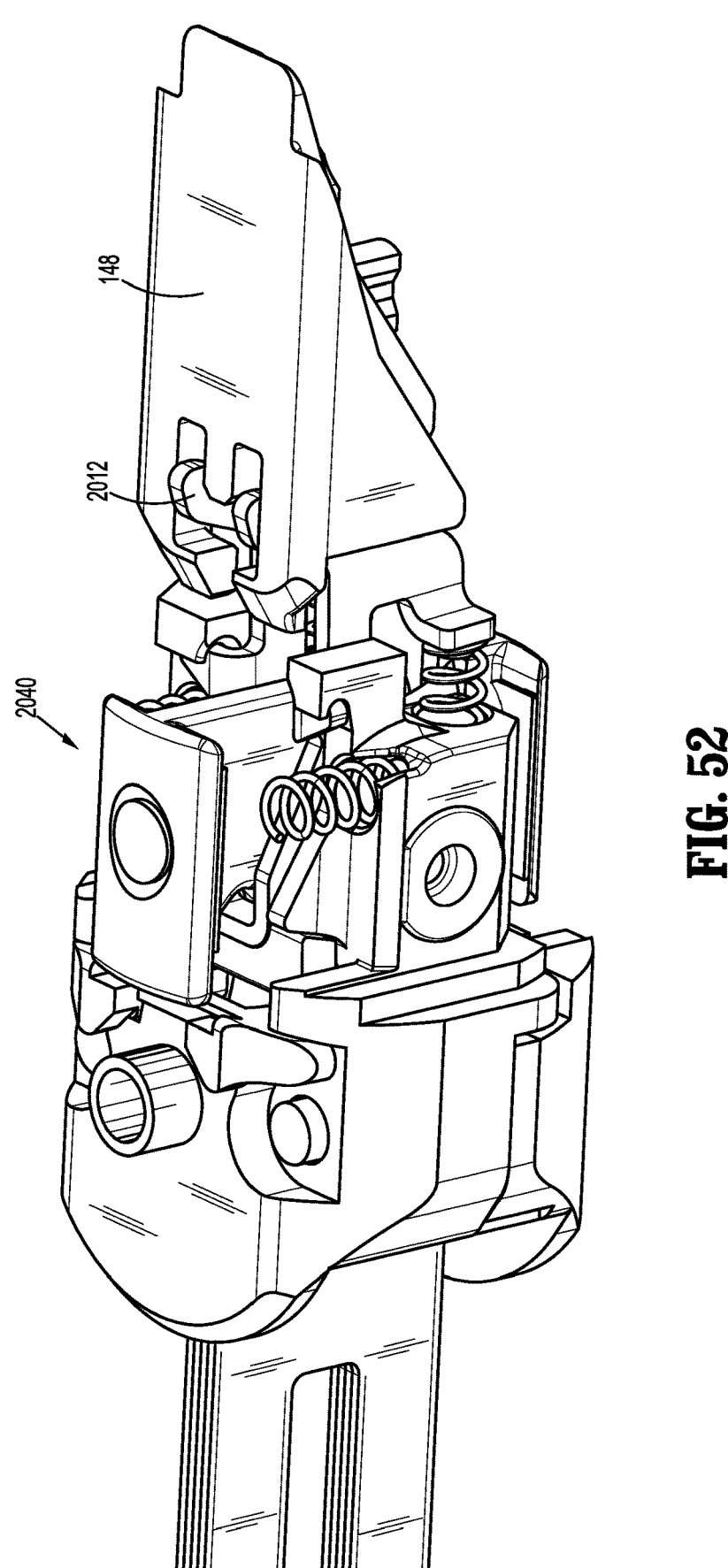
FIG. 52 is a perspective view of the loading unit with parts removed showing the lockout mechanism.
Figure 53:
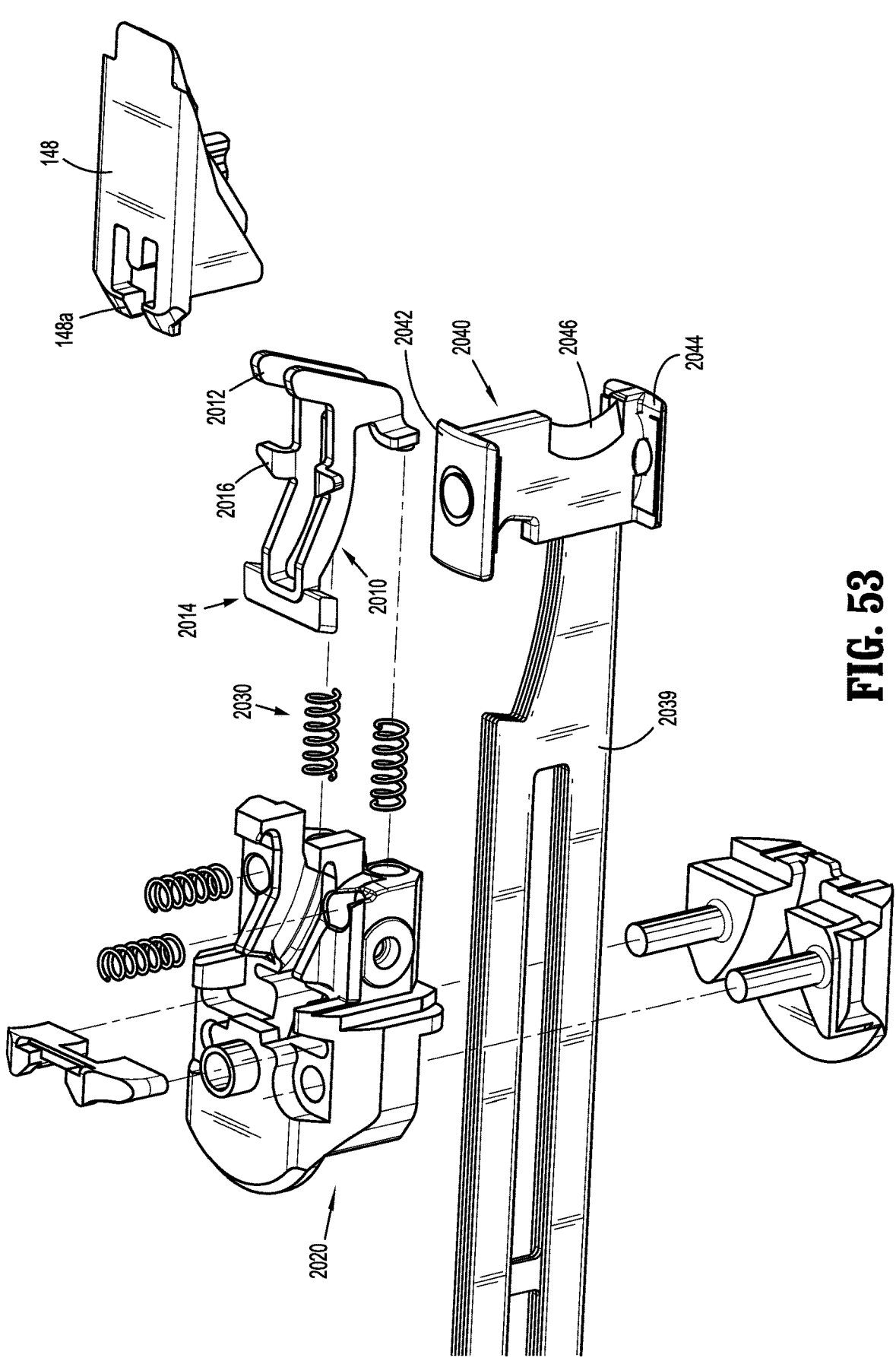
FIG. 53 is a perspective view of the lockout mechanism with parts separated showing the drive beam.
Figures 54, 55:
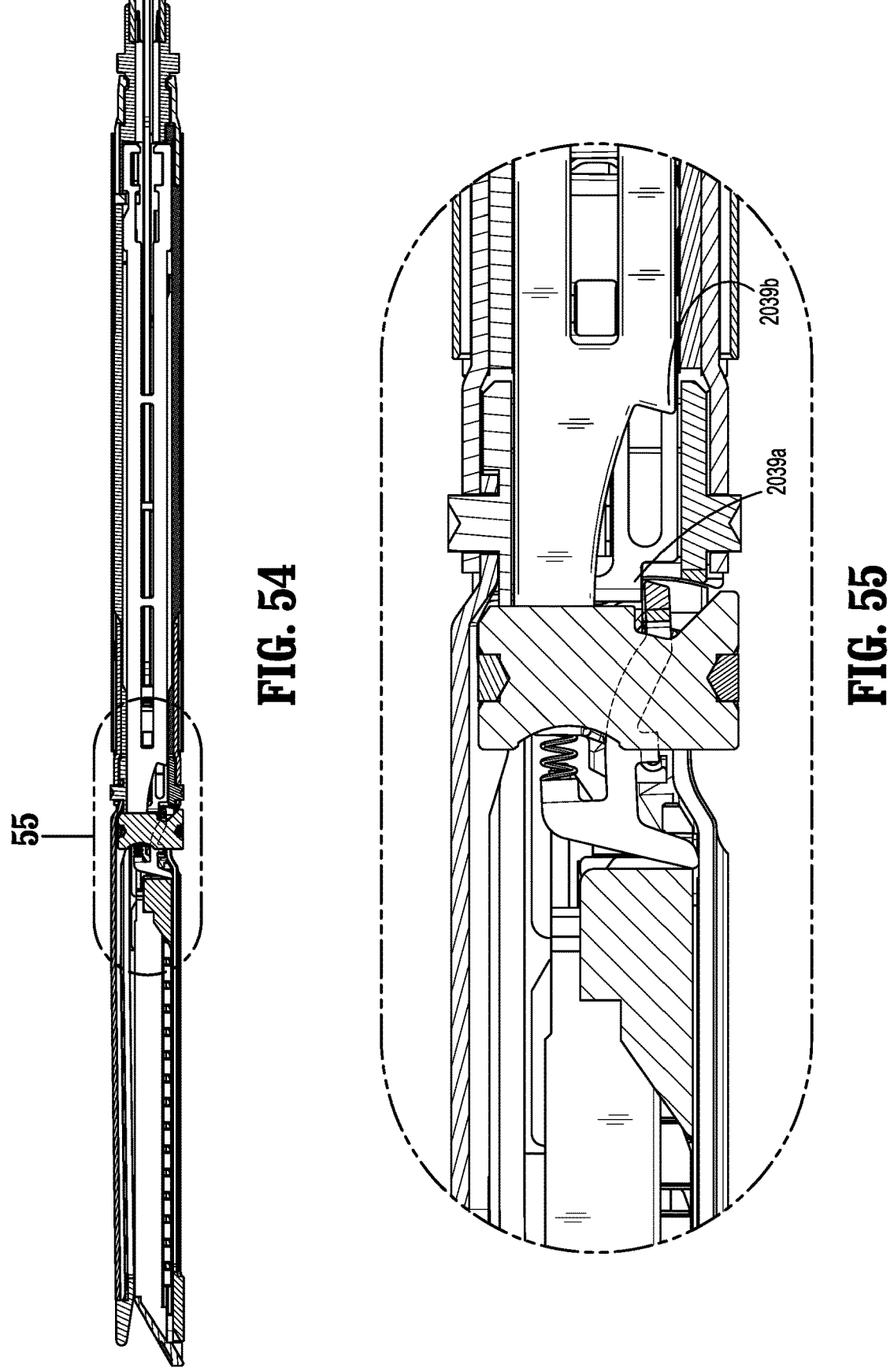
FIG. 54 is a cross sectional view taken longitudinally through the loading unit.
FIG. 55 is a detailed view of FIG. 54 showing the latch and dynamic clamping member.

The cartridge body 140 includes a central slot 143, and rows of staple retention slots positioned on each side of slot 143 (see FIG. 32). Cartridge body also includes a pair of engagement structures or protrusions which may, in certain embodiments, be slots or openings adjacent its proximal end for connection with the support plate 111a and/or channel 120.

With particular reference to FIG. 29, support plate 111a includes a base 145, engagement features 147 and 147a (see FIG. 38) for connection with the cartridge body and/or channel, and a mounting portion 149 at a proximal end thereof (see FIG. 29). The support plate 111a is disposed underneath the cartridge body to support the staple pushers, actuation sled, and staples (or other surgical fasteners) and prevent those components from falling out of the staple cartridge assembly.

The loading unit can include a chip assembly 360 mounted on a proximal end of the proximal body portion 118, as shown in FIGS. 41-45, for example. The chip assembly is as described above in connection with the authentication board assembly 30 discussed above. The chip assembly 360 is mounted for connection with a board assembly in the coupler on the distal end of the adapter assembly 114, and can be configured as discussed above in connection with FIGS. 1-21. The chip assembly 360 includes a chip 361 for authentication and information purposes, and can include a memory that stores certain information. The information can include the type of device the loading unit is, the version of the device/loading unit, the name of the loading unit, the manufacturing lot number, the serial or other identification number, the maximum force to which the drive beam of the loading unit can be driven, the interlock zone (mm), the end zone (mm), whether or not the loading unit can articulate, and/or a usage limit (the number of times the loading unit can be used). The interlock zone is the position of the drive beam, in millimeters, measured from the start or initial position of the drive beam, when the drive beam is engaged by a lockout in the loading unit. The end zone is the position of the drive beam, in millimeters, measured from the start or initial position of the drive beam, when the drive beam has reached the end of its travel in the staple cartridge body 140. Since the staple cartridge assembly 115 can be removed and replaced, there is an intended limit to the number of times the loading unit can be reloaded with a fresh unfired staple cartridge. The information stored on the chip can include the length of the staple line and/or cartridge.

The controller 121a in the handle assembly 112 can be programmed to read the information on the chip 361. This information is used in the operation of the surgical system. Desirably, some or all of the information is encrypted, which can be accomplished as discussed above in connection with FIGS. 1-21. The controller can be programmed to not provide power to a motor (not shown) disposed in the handle assembly 112, and not operate the adapter assembly and loading unit, in the event that the serial number or other data is not recognized. The maximum force information is used in conjunction with a load sensor, such as a strain gauge, disposed in the surgical system. For example, a load sensor can be disposed in the adapter assembly 114 and/or loading unit, such as a load sensor on the drive beam. The controller is programmed to compare the data from the load sensor to the maximum force data stored on the chip so that, for example, the operation of the motor (not shown) is interrupted before the maximum force is exceeded. In another example, the controller can be programmed to operate in "slow mode" if the measured force reaches a predetermined level. The predetermined level of force can be the maximum force discussed above, or another level of force, stored on a chip in the system, such as chip 361. Slow mode means that the controller operates the motor (not shown) at a slower rate, generating more torque, and also delaying the compression of tissue and/or firing of staples. In thick tissue, slow mode can allow fluid in the tissue to move away from the site of stapling, facilitating more compression of the tissue.

In a similar manner, the operation of the motor can be stopped or operated in slow mode if the drive beam is disposed in the interlock zone or the end zone. Furthermore, the controller can interrupt or prevent the operation of the articulation linkage, bar or cable if the data on chip 361 indicated that the loading unit does not articulate.

It is contemplated that the chip 361 with some or all of the data discussed above can be provided in any of the embodiments disclosed herein, including loading units that do not have a removable and replaceable staple cartridge assembly, and/or loading units that do not articulate.

It is contemplated that the information on chip 361 can be read by the controller in the handle assembly, another chip in the system, or any other computer component in the surgical system.

In any of the embodiments disclosed herein, the controller can write information to the chip on the loading unit. For example, the maximum force that was used to clamp onto tissue, as measured by the load sensor discussed above, the maximum force that was used to fire staples, and/or the position of the drive beam when the drive beam stops advancing, etc. Other information that can be written to the chip 361 includes the location of the drive beam when the device entered into slow mode, the number of times the loading unit has been fired, whether the loading unit has been fired, the type of handle assembly, the serial number of the handle assembly, the type of adapter assembly, and/or the serial number of the adapter assembly. The maximum force to fire staples can be saved along with the position of the drive beam, in any of the embodiments disclosed herein. The information can also be saved in a memory connected to the controller in the handle assembly, other chips in the system, or other computer components of the surgical system.

It is also envisioned, in any of the embodiments disclosed herein, that an end effector or tool assembly is arranged for articulating between a first position where tool assembly is aligned with longitudinal axis "Y-Y," and a second position where tool assembly is disposed at an angle with respect to longitudinal axis "Y-Y." For example, the tool assembly, which includes the anvil jaw member and the cartridge jaw member, may be mounted so as to be pivotable with respect to the proximal body portion 118. The anvil jaw member and cartridge jaw member can be attached to a mounting assembly 2020 (discussed further below), and the mounting assembly can be pivotably connected to the proximal body portion 118. The loading unit 116 includes one or more cables or linkages disposed in the proximal body portion so that when the cable or linkage is displaced, the tool assembly pivots and articulates with respect to the instrument. Further details of providing articulation are described in detail in commonly-owned U.S. Pat. No. 6,953,139 to Milliman et al., the contents of which are hereby incorporated by reference in their entirety. The adapter assembly 114 can include a linkage, bar or cable for enabling the articulation of the tool assembly.

As seen in FIG. 32, for example, any of the embodiments disclosed herein can include a cartridge body 140 having a stepped tissue-contacting surface 1412. In such embodiments, different sized staples, or all the same sized staples, may be used. Further details of a staple cartridge having multiple staple sizes are included in U.S. Pat. No. 7,407,075 to Holsten et al., the entire contents of which are hereby incorporated by reference herein. The staple forming recesses of the anvil, or the staple pushers, or both, can be configured accordingly, to form the staples in the desired shape and size.

Figure 27:
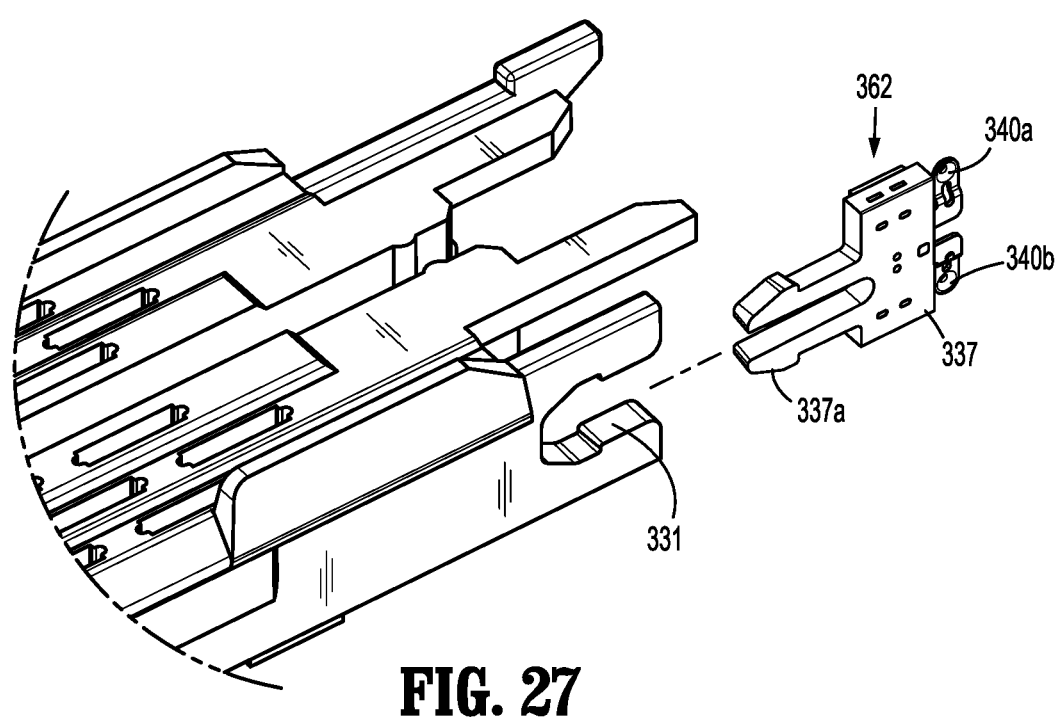
FIG. 27 is a detailed perspective view of a chip assembly.
Figure 28:
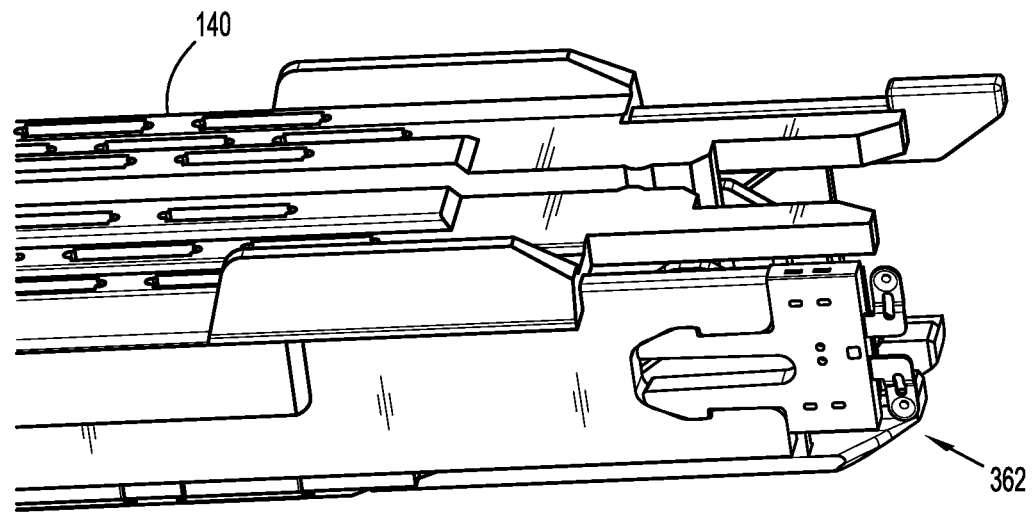
FIG. 28 is another detailed perspective view of the chip assembly of FIG. 27.

The removable and replaceable staple cartridge assembly 115 can further include a chip assembly 362. (see FIGS. 27 and 28). A corresponding board assembly 380 (FIGS. 25 and 26) is disposed on the tool assembly of the loading unit 116, and may be disposed on the channel 120. The tool assembly board assembly 380 can be configured as discussed above in connection with the adapter board assembly 50 of the adapter coupler 27. The tool assembly board assembly 380 is configured to be securely mounted on a wall of the channel 120. This board assembly 380 is positioned such that when cartridge assembly 140 is secured to the channel 120 of the loading unit, the chip assembly 362 engages the board assembly 380 mounted on the channel. (See FIGS. 29-31). FIGS. 27 and 28 show the relationship between the chip assembly and the staple cartridge body 140, whereas FIG. 29 shows the relationship between the chip assembly 362 and the support plate 111*a*.

In more detail, chip assembly includes a body 337 and a pair of contact members 340*a*, 340*b* (collectively, contact members 340) connected to a chip 336 disposed in the body. Body 337 defines a rectangular member having flexible arms with snap features 337*a* thereon. The flexible arms are configured to be securely received within a recess 331 defined by in the cartridge body. Chip 336 is in electrical communication with contact members 340.

Chip 336 includes any chip capable of storing information concerning the staple cartridge assembly 115. The chip can be the same or similar to the chip of the authentication board assembly 30. In any of the embodiments disclosed herein, any of the chips can store information such as, without limitation, cartridge size, staple arrangement, staple line length (or length of the cartridge), date of manufacture, expiration date, compatibility characteristics, a unique identifier (e.g., a serial number), and/or number of uses, as well as whether or not the staple cartridge assembly has been used. Such information can be transmitted to the controller in the handle assembly 112, or to another computer component through an appropriate bus, pin connection, wireless means, etc. In some embodiments, chip 336 includes an erasable programmable read only memory ("EPROM") chip. The controller in the handle assembly can write information to the chip 336. In this manner, the handle assembly 112 may adjust the firing forces, firing stroke, and/or other operational characteristics thereof in accordance with the information concerning the staple cartridge assembly that are transmitted from chip 336. The handle assembly 112 can communicate to chip 336 that the staple cartridge assembly has been used, which can prevent reloading or reuse of an expended reload assembly, or any other unauthorized use. The information stored in any of the components in the surgical system can be encrypted using private keys, public keys, and/or secure hash algorithms.

The board assembly 380 also has a pair of contacts 380*a* and 380*b* and a body 381. The board assembly is mounted for contact with the chip assembly 362 when the staple cartridge assembly is properly mounted in the channel 120. The contacts 380*a*, 380*b*, 340*a*, and 340*b* have an L-shaped configuration as seen in the figures so that they may resiliently engage one another. The body 381 can define a snap feature 382 that is provided to engage a hole 383 in the channel to securely mount the board assembly. The board assembly is appropriately connected to a bus, wires, or has a wireless communicator for transmittal of the information from chip assembly 362 to the controller in the handle assembly, or any other computer device.

In any of the embodiments disclosed herein, a lockout mechanism 500 is disposed in the loading unit. The loading unit may be configured as discussed above. Furthermore, the present disclosure is directed to a removable assembly having the lockout, or a loading unit having the lockout.

The lockout mechanism 500 includes a latch 2010 and at least one spring 2030, and is configured to prevent re-firing of a staple cartridge assembly 115 or staple cartridge 26, and also prevent distal translation of a drive beam after the staple cartridge has been fired and prior to loading of another cartridge assembly 115. The lockout mechanism 500 is shown alongside the sled 148 and mounting assembly 2020 in FIG. 50. The at least one spring 2030 is mounted on a distally facing surface 2031. For example, recesses are formed in surface 2031 for receiving springs 2030. Corresponding posts are provided on a proximally facing surface of the latch 2010. The latch is configured to be pivotable within the loading unit, and includes at least one prong 2012, a rear portion 2014, and a supporting portion 2016. The latch is configured to pivot around the supporting portion 2016, shown in FIGS. 50 and 51 as two downwardly depending features, and is biased by the spring or springs 2030. The sled 148 has a hole or recess for receiving the at least one prong 2012 when the latch and drive beam are in their initial positions. (see FIG. 52). The drive beam 2039 can interact with, or include, a dynamic clamping member 2040 having an upper flange 2042, lower flange 2044, and knife blade 2046. (see FIG. 53).

In the initial position, the latch 2010 is biased in a forward or distal direction, with the rear portion 2014 in contact with an edge 2039a on the drive beam 2039, preventing further rotational movement of the latch. As the drive beam and dynamic clamping member are moved in a forward or distal direction, the dynamic clamping member pushes the sled distally. A rear portion 148a of the sled pushes the prong or prongs 2012, tilting the latch against the bias of the at least one spring 2030. This removes the rear portion 2014 from the area near the edge 2039a, and allows the drive beam and dynamic clamping member to move forward. After the dynamic clamping member passes the latch 2010, the latch rotates forwardly under the influence of the spring. (see FIG. 57).

After the dynamic clamping member and sled have fired the staples from the cartridge 140, the dynamic clamping member is moved proximally, leaving the sled at the distal end of the cartridge 140 and cartridge assembly 115. The dynamic clamping member can move past the latch 2010, as cam surface 2041 moves the latch out of the path of travel (see FIG. 57). Once the dynamic clamping member returns to the initial position, the latch 2010 will prevent another forward movement of the dynamic clamping member 2040. The latch rear portion 2014 is in a position to engage another edge 2039b of the drive beam. (see FIG. 57). If the loading unit is of the type that accepts removable and replaceable staple cartridge assemblies 115, the cartridge assembly 115 can be configured to return the latch 2010 to the initial position, so that the drive beam and dynamic clamping member can again be moved distally to fire another set of staples.

As discussed above, any of the embodiments disclosed herein can include a chip assembly 360 on a surgical stapling loading unit, like loading unit 116 that has information on it concerning the lockout mechanism, such as the lockout mechanism discussed above. Furthermore, information can be stored on the chip 361 concerning the lockout mechanism. For example, the fact that the lockout mechanism was engaged can be recorded in chip assembly 360 and/or chip assembly 362 by the controller in the handle. The controller in the handle can include a memory for storing information, including a processor, and other computer components. The controller can also include a current meter, or ammeter, to measure the current in the motor of the handle assembly. The controller can be programmed to record the peak current reached during use of the loading unit and/or staple cartridge assembly, and can record that peak current on any of the chips or other computer components in the system. A peak current reached after the staples have been fired can be an indication that the loading unit was attempted to be fired a second time before a fresh staple cartridge assembly was mounted in the loading unit. Alternatively, the lockout mechanism can include a sensor such as, for example, on the latch. It is contemplated that the surgical system can include loading units that do not have a lockout mechanism like the one discussed above. The fact that the loading unit does not have a lockout mechanism can be stored in chip 361.

The handle assembly can also include an encoder that determines how many rotations of the motor output shaft have been made, which can be used to determine a position of drive bars, linkages, cables, etc., in the adapter assembly, the drive beam or firing bar in the loading unit, or other components. Alternatively, other sensors can be used to determine the position of various components in the surgical system.

The adapter assembly disclosed herein, in any of the embodiments disclosed herein, can be configured as disclosed in U.S. Published Application No. 2011/0174099 A1, the entire disclosure of which is hereby incorporated by reference herein. The motor in the handle assembly provides a rotational output on a rotating shaft and the adapter is configured to transform that output to a linearly moving linkage or bar, and can also provide drive to an articulation linkage in the proximal body portion 118 of the loading unit 116. The handle assembly and/or adapter assembly can be configured as disclosed in U.S. Published Application Nos. 2014/0012289 A1 and 2014/0110453 A1, the entire disclosures of which are hereby incorporated by reference herein.

Force Measurement and Drive Circuit

Any of the embodiments disclosed herein can include a force measurement and drive circuit, or be configured to be used with a component that has a force measurement and drive circuit. Surgical instruments for applying fasteners are known wherein the force exerted on an end-effector assembly by the motor drive mechanism has been estimated by motor current measurements. However, there may be sources of error in this measurement scheme that change with temperature, and there are uncertainties due to the differences in friction between one end-effector assembly and adapter combination and another end-effector assembly and adapter combination, which mean that the forces estimated by motor currents alone are variable in their reliability.

Various embodiments of the present disclosure provide a surgical instrument including an adapter configured to operably couple the end-effector assembly to a motor drive mechanism and configured to directly measure a driving force in the adapter. The presently-disclosed surgical instrument embodiments are capable of detecting excessive loads and/or preventing damage to the adapter and/or a handle assembly, which may increase reliability. Various embodiments of presently-disclosed surgical instrument are also capable of collecting data related to tissue compression. The presently-disclosed surgical instrument embodiments are configured to accurately determine when a tissue end stop or end stop condition has been reached.

Various embodiments of presently-disclosed surgical instrument utilize an adapter configured with a strain gauge and a drive circuit. Although the following description describes the use of a strain gauge, the teachings of the present disclosure may also apply to a variety of sensing devices capable of providing an electrical output proportional to applied pressure. In some embodiments, the drive circuit includes a dedicated instrumentation amplifier, custom tuned 2-pole filter, low power mode switch, 12 bit analog-to-digital converter, and 32 bit microprocessor. Although the following description describes the use of a surgical instrument for applying surgical staples, the teachings of the present disclosure may also apply to a variety of surgical devices that include an end-effector assembly and a shaft, e.g., devices that seal tissue.

Figure 58:
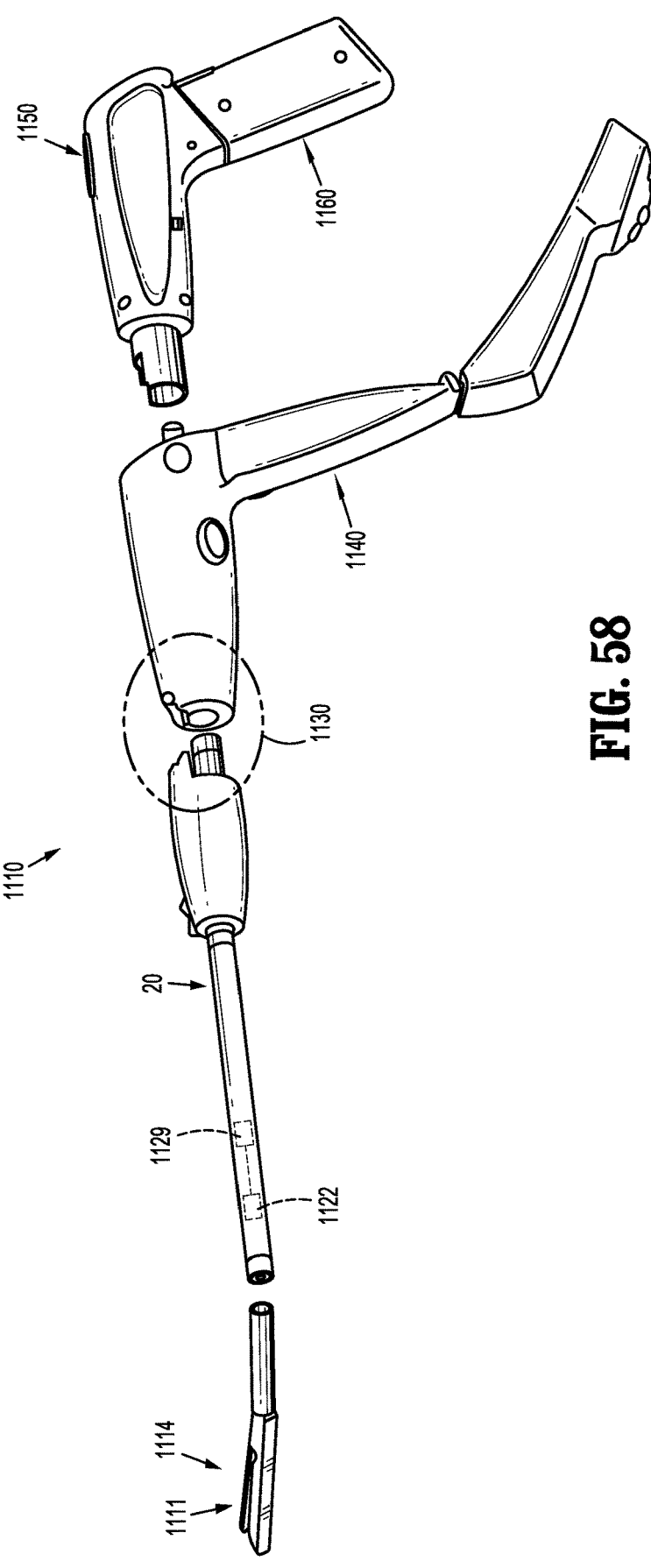
FIG. 58 is a perspective view of a surgical instrument for applying surgical staples, shown with parts separated, including an adapter configured with a strain gauge and a drive circuit according to an embodiment of the present disclosure.

FIG. 58 shows a surgical instrument 1110 for use in various surgical procedures, e.g., endoscopic surgical procedures, and includes a motor pack 1150, a battery pack 1160, an adapter 1120, and a replaceable loading unit 1114 having an end-effector assembly 1111 configured to apply staples. Replaceable loading unit 1114 and/or the end-effector assembly 1111 may include staples of various sizes and the staples may be arranged in one or more configurations. In some embodiments, the replaceable loading unit 1114 is configured to be releaseably coupled to a distal end of the adapter 1120.

As shown in FIG. 58, surgical instrument 1110 includes a clamshell 1140 configured to hold the motor pack 1150 and the battery pack 1160, and includes a coupling mechanism 1130 for operably coupling the adapter 1120 via the clamshell 1140 to the motor pack 1150. Surgical instrument 1110 may additionally, or alternatively, include a handle assembly (not shown) wherein the adapter 1120 extends from the distal end of the handle assembly. In some embodiments, the instrument 1110 may be provided with a transmission line (not shown) for connecting the instrument 1110 to an external power source.

In accordance with embodiments of the present disclosure, the driving force is measured directly in the adapter 1120 using a strain gauge 1122, or other force sensor, and a drive circuit 1129 operably associated therewith. Embodiments of the presently-disclosed surgical instrument 1110 may include factory-calibrated force measurements whereby the slope and offset correction factors are permanently stored in the microprocessor (e.g., microprocessor 1240 shown in FIGS. 59 and 60) of the drive circuit 1129. In this way, adapters 1120 can be interchanged between different handle assemblies, or clamshells 1140, and the calibrated force measurements are assured. In some embodiments, calibrated force measurements at the end of stroke will rise, which helps to allow for reliable end-stop detection.

Force sensors and force transducers may exhibit a drift of offset with temperature and over time. In accordance with embodiments of the present disclosure, force transducers are calibrated at the factory during manufacture. This calibration provides correction factors to the microprocessor (e.g., microprocessor 1240 shown in FIGS. 59 and 60) for use by the microprocessor to modify the data received from the transducer (e.g., strain gauge 1122) to match the real world forces that are applied during factory manufacturing. In an illustrative embodiment, the calibration first entails a measurement of the transducer offset "Y1." Next, a known force "F1" is applied to the transducer, and the output of the transducer is measured to provide a data point "Y2." The apparent slope "Sapp" may be calculated using the equation Sapp=(Y2−Y1)/F1.

The offset "Y1" may be stored in the microprocessor 1240 (and/or stored in memory operably associated therewith), and the microprocessor 1240 may be configured to subtract the offset "Y1" from all data received from the transducer. This represents a "b" correction for the straight line expected from the transducer using the y=mx+b equation. The slope correction may be calculated by first comparing "Sapp" to the ideal value "Si" that is the ideal output of the system with a force "F1" input. The term "m" in the y=mx+b equation is modified by the ratio Si/Sapp.

Figure 59:
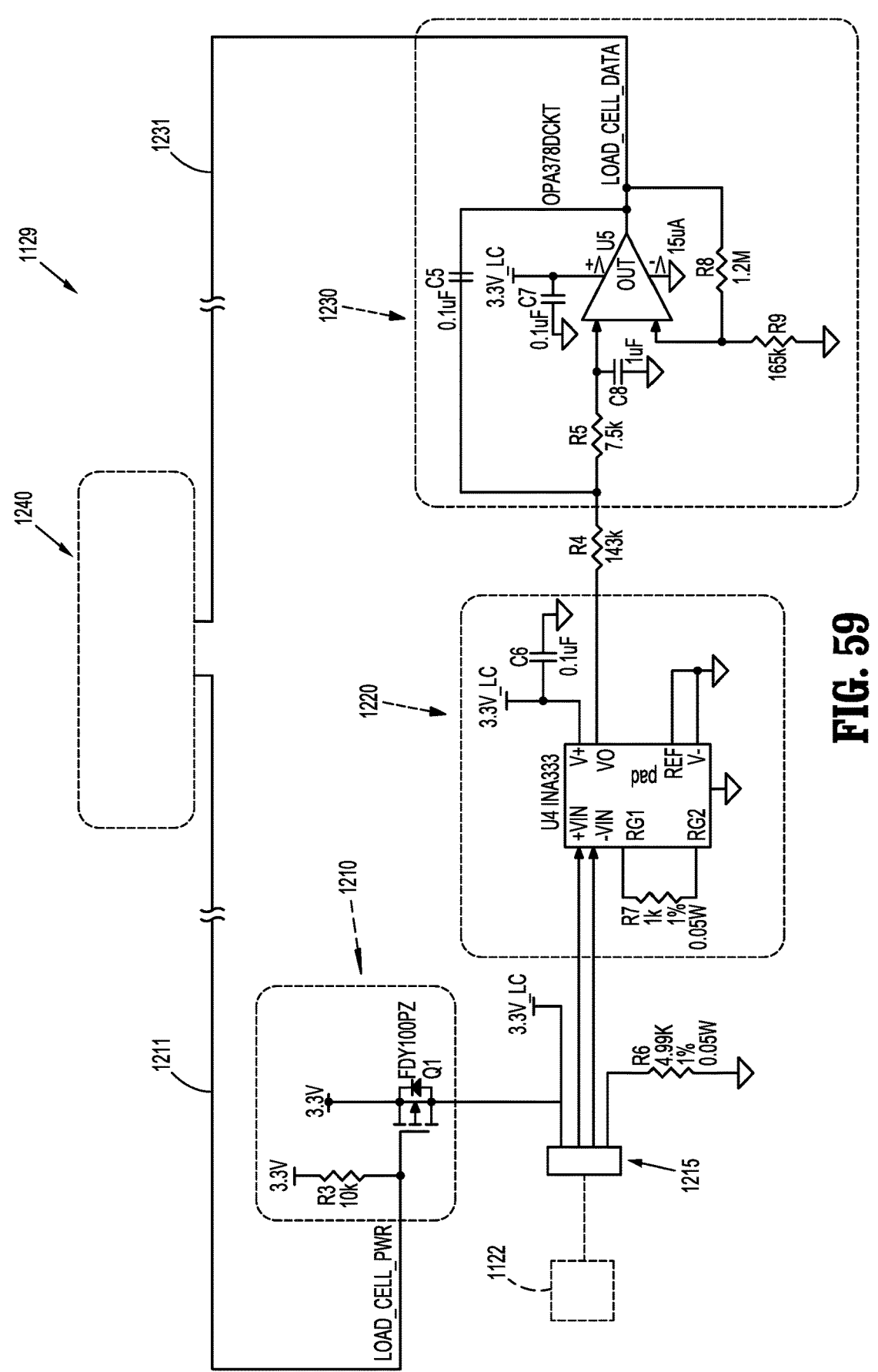
FIG. 59 is a circuit diagram of the drive circuit of FIG. 1 according to an embodiment of the present disclosure.
Figure 60:
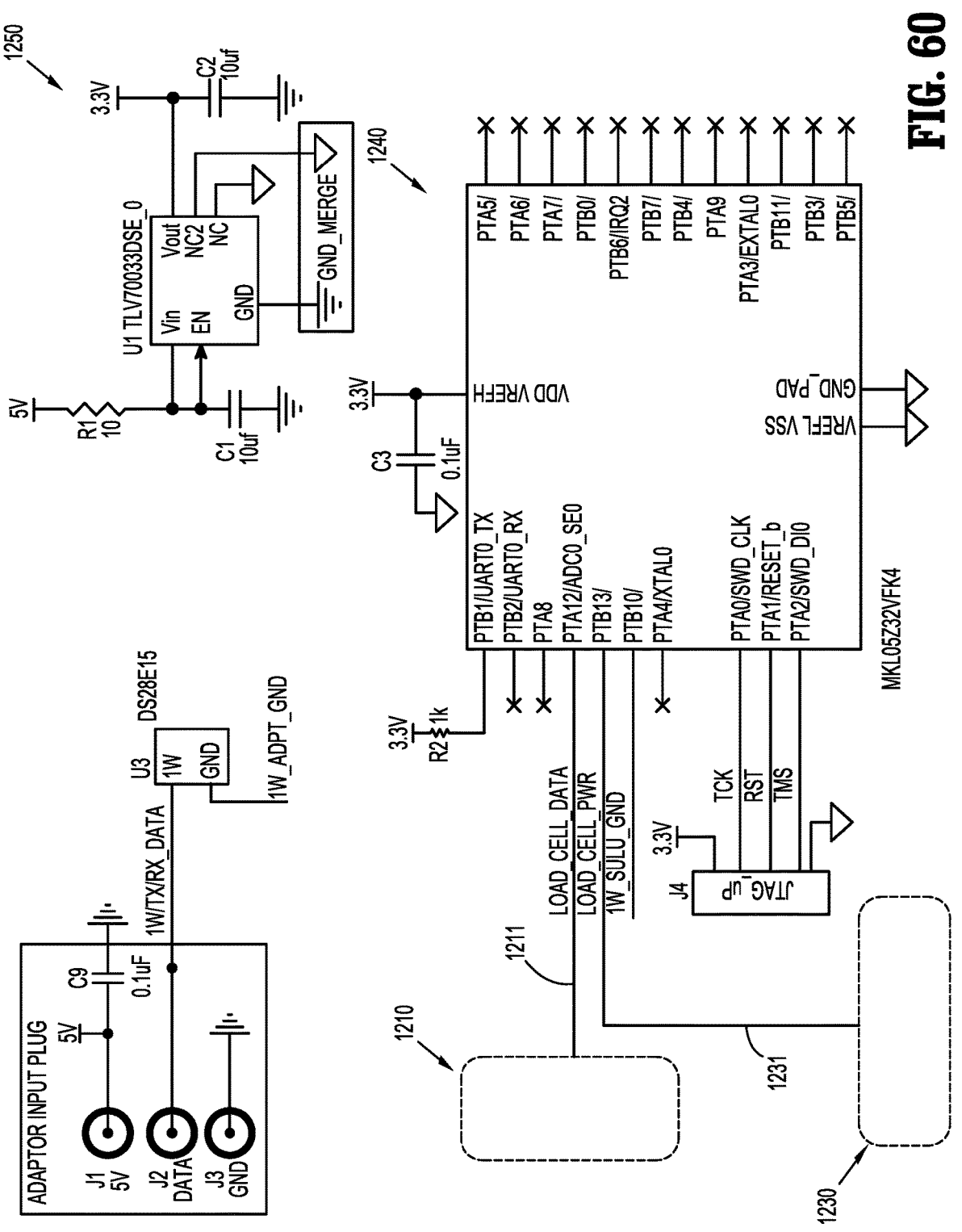
FIG. 60 is a circuit diagram showing the microprocessor of FIG. 2 and a voltage regulation circuit according to an embodiment of the present disclosure.

In FIGS. 59 and 60 a circuit diagram of the drive circuit 1129 (FIG. 58) is shown and includes an instrumentation amplifier 1220, a microprocessor 1240, an operational amplifier or "op-amp" 1230, and an interface 1215, which is connected to the strain gauge 1122, and power on/off circuit 1210 providing on/off capability. As shown in FIG. 60, the drive circuit 1129 further includes a voltage regulation circuit 1250, which provides clean DC voltage. In some embodiments, voltage regulation circuit 1250 provides a DC voltage of 3.3 volts.

Instrumentation amplifier 1220 is selected for power supply injection ratio and no current consumption. Instrumentation amplifier 1220 is designed to boost a relatively noisy signal or a very weak signal that comes from the strain gauge, e.g., boost the signal about 50 times. Op-amp 1230 generally has low current draw and small size, and may be configured to boost the signal from the amplifier 1220 about 10 times. In some embodiments, op-amp 1230 provides 20 dB of gain with 20 Hz cut-off frequency, and may be a two pole Butterworth filter. Op-amp 1230 may also provide low-pass filtering, e.g., to reject motor noise, and/or may provide electromagnetic interference (EMI) suppression. The analog output of the op-amp 1230 is transmitted via conductor 231 to the analog-to-digital input of the microprocessor 1240 and converted to digital form. Due to space constraints for housing the drive circuit 1129 within the adapter 1120, one of the main considerations in selecting an op-amp 1230 and a microprocessor 1240 is small size.

Hereinafter, a method of measuring a driving force in a surgical device in accordance with the present disclosure is described with reference to FIG. 61. It is to be understood that the steps of the method provided herein may be performed in combination and in a different order than presented herein without departing from the scope of the disclosure.

FIG. 61 is a flowchart illustrating a method of measuring a driving force in a surgical device in accordance with an embodiment of the present disclosure. In step 1410, a surgical instrument 1110 is provided and includes an adapter 1120 configured to releaseably couple a replaceable loading unit 1114 having an end-effector assembly 1111 to a drive motor 1150. Adapter 1120 includes a strain gauge 1122 coupled to a drive circuit 29 capable of detecting excessive loads. In some embodiments, the end-effector assembly is configured to apply staples.

In some embodiments, the drive circuit 1129 includes a microprocessor 1240 and an op-amp 1230. Op-amp 1230 may be configured to provide low-pass filtering and/or may be a two pole Butterworth filter. In some embodiments, the method illustrated in FIG. 61 may further include transmitting an analog output of the op-amp 1230 to an analog-to-digital input of the microprocessor 1240. Drive circuit 1129 may further include a voltage regulation circuit 1250, which may provide a DC voltage of 3.3 volts.

In step 1420, the strain gauge 1122 and the drive circuit 1129 are used to directly measure a driving force in the adapter 1120 to obtain a force measurement.

In step 1430, if it is determined based on the force measurement that an excessive load has been detected, the driving force is adjusted to prevent damage to the adapter 1120.

In some embodiments, the method illustrated in FIG. 61 may further include applying staples using the end-effector assembly and/or utilizing the end-effector assembly 1111 in endoscopic surgical procedures.

The above-described surgical instruments and method of measuring a driving force in a surgical device may be suitable for utilization in endoscopic surgical procedures and/or suitable for utilization in open surgical applications.

Figures 56, 57:
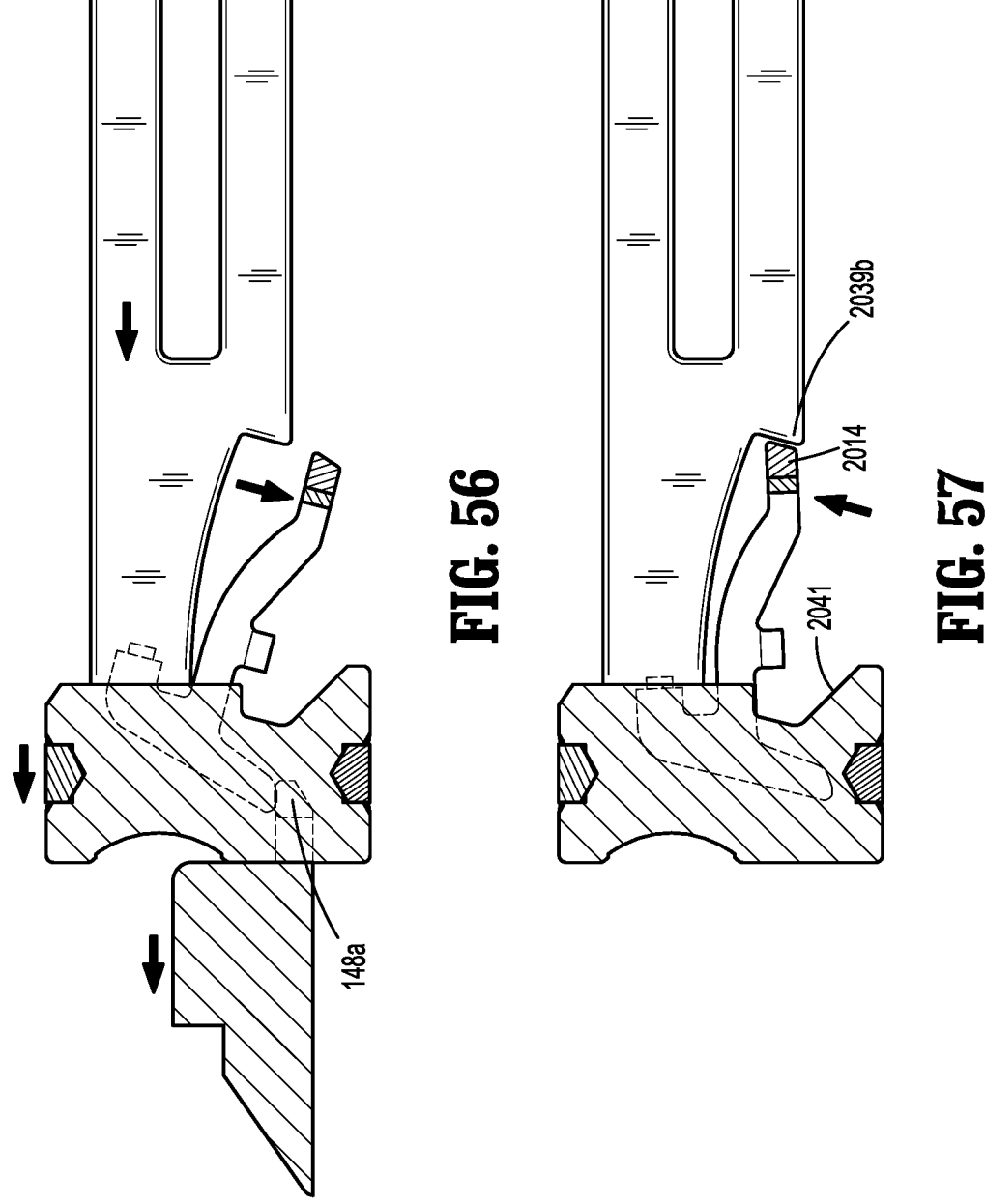
FIG. 56 is a side view of the drive beam, dynamic clamping member, and sled.
FIG. 57 is a side view of the drive beam, dynamic clamping member, and sled, with the drive beam and dynamic clamping member advanced.

Any of the embodiments described in connection with FIGS. 1 through 57 can include the strain gauge (or other force sensor) and/or the drive circuit discussed above. In any of the embodiment disclosed herein, the motor in the handle assembly or clamshell may be any electrical motor configured to actuate one or more drives (such as rotatable drive connectors). The motor is coupled to a battery, which may be a DC battery (e.g., rechargeable lead-based, nickel-based, lithium-ion based, battery etc.), an AC/DC transformer, or any other power source suitable for providing electrical energy to the motor.

Although embodiments have been described in detail with reference to the accompanying drawings for the purpose of illustration and description, it is to be understood that the disclosed processes and apparatus are not to be construed as limited thereby. For example, the strain gauge or other force sensor can be provided on the drive beam, dynamic clamping member, anvil, or other components in the surgical system. It will be apparent to those of ordinary skill in the art that various modifications to the foregoing embodiments may be made without departing from the scope of the disclosure.

What is claimed is:

1. A surgical instrument, comprising:
an adapter assembly having a proximal end portion configured to be removably coupled to a handle assembly;
a loading unit configured to be removably coupled to a distal end portion of the adapter assembly, the loading unit including:
an end effector disposed at a distal end portion of the loading unit and configured for treating tissue; and
an adapter coupler disposed at a proximal end portion of the loading unit and configured to be coupled to the distal end portion of the adapter assembly; and
an electrically conductive contact assembly disposed on the adapter coupler and configured to electrically couple the loading unit to the adapter assembly, the contact assembly including:
a contact base;
a first contact arm extending proximally from the contact base; and
a second contact arm extending proximally from the contact base further than the first contact arm such that a proximal end of the second contact arm is disposed proximal to a proximal end of the first contact arm, wherein at least one of the first or second contact arms includes a tab configured to electromechanically couple the contact assembly to a circuit board disposed on the proximal end portion of the loading unit.

2. The surgical instrument according to claim 1, wherein the tab is orthogonally disposed on a lower portion of a distal end of at least one of the first or second contact arms.

3. The surgical instrument according to claim 1, wherein the contact assembly is electrically coupled to a chip disposed on the proximal end portion of the loading unit, the chip having a memory storing data associated with the loading unit.

4. The surgical instrument according to claim 3, wherein the data associated with the loading unit is selected from the group consisting of a cartridge size, a staple arrangement, a staple length, a clamp-up distance, a date of manufacture, an expiration date, a compatibility characteristic, a unique identifier, and a number of uses.

5. The surgical instrument according to claim 1, wherein the first contact arm includes a first contact member orthogonally disposed on an upper portion of a proximal end of the first contact arm and the second contact arm includes a second contact member orthogonally disposed on an upper portion of a proximal end of the second contact arm.

6. The surgical instrument according to claim 5, wherein the first contact member and the second contact member are aligned with each other along a longitudinal axis defined by the contact assembly.

7. The surgical instrument according to claim 1, wherein the first and second contact arms extend from the contact base parallel to each other.

8. The surgical instrument according to claim 1, wherein the surgical instrument is a surgical stapling device.

9. A loading unit for a surgical instrument, comprising:
a body portion extending between a proximal end portion and a distal end portion;
an end effector disposed at the distal end portion of the body portion;
an adapter coupler disposed at the proximal end portion of the body portion and configured to operably couple the body portion to a handle assembly to enable actuation of the end effector via the handle assembly; and
an electrically conductive contact assembly disposed on the adapter coupler and configured to electrically couple the loading unit to the handle assembly, the contact assembly including:
a first contact arm having a first contact member;
a second contact arm joined to the first contact arm and having a second contact member aligned with the first contact member along a longitudinal axis defined by the electrically conductive contact assembly, wherein:
the first contact member and the second contact member extend orthogonally to the first contact arm and second contact arm;
the first contact member extends from the first contact arm in a first direction; and
the second contact member extends from the second contact arm in a second direction that is opposite the first direction.

10. The loading unit according to claim 9, wherein a distal end of the first contact arm is joined to a distal end of the second contact arm by a contact base.

11. The loading unit according to claim 10, wherein the second contact arm extends proximally from the contact base further than the first contact arm such that a proximal end of the second contact arm is disposed proximal to a proximal end of the first contact arm.

12. The loading unit according to claim 10, wherein the first and second contact arms extend from the contact base parallel to each other.

13. The loading unit according to claim 9, wherein at least one of the first or second contact arms includes a solder tab configured to electromechanically couple the contact assembly to a circuit board disposed on the adapter coupler.

14. The loading unit according to claim 13, wherein the solder tab is orthogonally disposed on a lower portion of a distal end of at least one of the first or second contact arms.

15. The loading unit according to claim 9, wherein the contact assembly is electrically coupled to a chip disposed on the proximal end portion of the loading unit, the chip having a memory storing data associated with the loading unit.

16. The loading unit according to claim 9, wherein the contact assembly is electrically coupled to a chip disposed on the adapter coupler, the chip having a memory storing data associated with the loading unit.

17. The loading unit according to claim 9, wherein the first contact member is orthogonally disposed on an upper portion of a proximal end of the first contact arm and the second contact arm includes the second contact member orthogonally disposed on an upper portion of a proximal end of the second contact arm.

18. The loading unit according to claim 9, wherein the loading unit is configured for use with a surgical stapling device.

\* \* \* \* \*